(12) United States Patent
Lopez-Calle et al.

(10) Patent No.: US 11,391,655 B2
(45) Date of Patent: Jul. 19, 2022

(54) GENERIC PRETREATMENT REAGENTS FOR ANALYTE DETERMINATIONS

(71) Applicant: Roche Diagnostics Operations, Inc., Indianapolis, IN (US)

(72) Inventors: Eloisa Lopez-Calle, Ludwigshafen (DE); Ewelina Hegel, Mannheim (DE); Thomas Fischer, Rauenberg (DE); Caroline Bylda, Oberhausen (DE); Hans-Peter Josel, Weilheim (DE); Josef Roedl, Mutterstadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 193 days.

(21) Appl. No.: 16/569,700

(22) Filed: Sep. 13, 2019

(65) Prior Publication Data

US 2020/0003666 A1   Jan. 2, 2020

Related U.S. Application Data

(63) Continuation of application No. PCT/EP2018/057754, filed on Mar. 27, 2018.

(30) Foreign Application Priority Data

Mar. 28, 2017 (EP) .................... 17163332

(51) Int. Cl.
*G01N 1/40* (2006.01)
*G01N 33/74* (2006.01)
*G01N 33/82* (2006.01)
*G01N 33/94* (2006.01)

(52) U.S. Cl.
CPC ......... *G01N 1/4044* (2013.01); *G01N 1/4055* (2013.01); *G01N 33/743* (2013.01); *G01N 33/82* (2013.01); *G01N 33/9493* (2013.01); *G01N 2001/4061* (2013.01); *Y10T 436/107497* (2015.01)

(58) Field of Classification Search
CPC .......... G01N 1/00; G01N 1/40; G01N 1/4044; G01N 1/4055; G01N 2001/4061; Y10T 436/107497
USPC ........................................................ 436/17
See application file for complete search history.

(56) References Cited

U.S. PATENT DOCUMENTS

| 7,964,363 | B2 | 6/2011 | Armbruster et al. | |
|---|---|---|---|---|
| 8,221,986 | B2 | 7/2012 | Grenier et al. | |
| 2005/0079535 | A1* | 4/2005 | Kirchgesser | C12N 15/1006 435/6.12 |
| 2013/0078729 | A1 | 3/2013 | Antoni et al. | |
| 2014/0273021 | A1 | 9/2014 | Zielinski et al. | |
| 2015/0355202 | A1 | 12/2015 | Uchida et al. | |
| 2017/0121702 | A1* | 5/2017 | Kirsch | C07H 1/06 |

FOREIGN PATENT DOCUMENTS

| JP | 2013529304 A | 7/2013 |
|---|---|---|
| WO | 2014122972 A1 | 8/2014 |

OTHER PUBLICATIONS

Tickler, A.K. et al. Overview of Solid Phase Synthesis of "Difficult Peptide" Sequences. Current Protocols in Protein Science 18.8.1-18.8.6, Nov. 2007. DOI: 10.1002/0471140864.ps1808s50. (Year: 2007).*
Al-Jenoobi, F.I. et al., Quantification of Immunosuppressant's in Blood using LC-MS/MS, Austin Chromatography, 2016, 11 pp., vol. 3, Issue 1, ID 1039.
Antignac, Jean-Philippe et al., The ion suppression phenomenon in liquid chromatography-mass spectrometry and its consequences in the field of residue analysis, Analytica Chimica Acta, 2005, pp. 129-136, vol. 529.
Chiu, May L. et al., Matrix Effects—A Challenge Toward Automation of Molecular Analysis, JALA: Journal of the Association of Laboratory Management, 2010, pp. 233-242, vol. 15.
Doyle, Rory, Sample Preparation and Ionization Mode Comparison Study for the Quantification of 25-Hydroxy Vitamin D2/D3 by LC/MS/MS for Clinical Research, Agilent Technologies, 2011, 46 pp.
Furey, Ambrose et al., Ion suppression; A critical review on causes, evaluation, prevention and applications, Talanta, 2013, pp. 104-122, vol. 115.
Gomes, Fabio P. et al., Recent trends in the determination of vitamin D, Bioanalysis, 2013, 2 pp., vol. 5, No. 24 (abstract only).
Henion, Jack et al., Sample Preparation for LC/MS/MS, Analytical Chemistry News & Features, 1998, pp. 650A-656A.
International Search Report dated Apr. 25, 2018, in Application No. PCT/EP2018/057754, 3 pp.
LGC Group, Guide to achieving reliable quantitative LC-MS measurements, None, 2013, 68 pp., http://www.rsc.org/images/AMC LCMS Guide_tcm18-240030.
Liu, Guowen and Aubry, Anne-Francoise, Best Practices in Biological Sample Preparation for LC-MS Bioanalysis, Handbook of LC-MS Bioanalysis: Best Practices, Experimental Protocols, and Regulations, 2013, 3 pp., Chapter 14 Summary, John Wiley & Sons Inc., Hoboken, NJ.
Marston, Fiona A. O. and Hartley, Donna L., Solubilization of Protein Aggregates, Methods in Enzymology, 1990, pp. 264-276, vol. 182, No. 20.

(Continued)

*Primary Examiner* — Jennifer Wecker
*Assistant Examiner* — Michelle Adams
(74) *Attorney, Agent, or Firm* — Stinson LLP

(57) ABSTRACT

The present disclosure relates to an in vitro method for releasing analytes from a sample involving contacting the sample with (i) a chaotropic agent, (ii) an organic solvent, (iii) a detergent, and (iv) at least one agent providing bicarbonate ions. The present disclosure further relates to a release agent for releasing analytes from a sample having the aforesaid compounds. Moreover, the present disclosure relates to uses, kits, methods and devices related to the method and the release agent of the present disclosure.

4 Claims, 3 Drawing Sheets

(56) References Cited

OTHER PUBLICATIONS

Peterson, Per A., Isolation and Partial Characterization of a Human Vitamin D-binding Plasma Protein, The Journal of Biological Chemistry, 1971, pp. 7748-7754, vol. 246, No. 24.
Proc, Jennifer L. et al., A Quantitative Study of the Effects of Chaotropic Agents, Surfactants, and Solvents on the Digestion Efficiency of Human Plasma Proteins by Trypsin, Journal of Proteome Research, 2010, pp. 5422-5437, vol. 9.
Roche Diagnostics GmbH, Cyclosporine, Package Insert for cobas® Elecsys 2010, Jun. 2013, 6 pp., V 1.0.
Roche Diagnostics GmbH, Everolimus, Package Insert for cobas® Modular Analytics E170, Nov. 2015, 5 pp., V 1.0.
Roche Diagnostics GmbH, ISD Sample Pretreatment, Package Insert for cobas® Elecsys 2010, Oct. 2014, 2 pp., V 3.0.
Roche Diagnostics GmbH, Sirolimus, Package Insert for cobas® Modular Analytics E170, Dec. 2015, 5 pp., V 1.0.
Roche Diagnostics GmbH, Tacrolimus, Package Insert for cobas® Elecsys 2010, Nov. 2014, 6 pp., V 3.0.
Roche Diagnostics GmbH, Testosterone II, Package Insert for cobas® Elecsys 2010, Dec. 2014, 6 pp., V 8.0.
Roche Diagnostics GmbH, Vitamin D total, Package Insert for cobas® Elecsys 2010, Nov. 2014, 5 pp., V 5.0.
Rommerts, F.F.G., Testosterone: an overview of biosynthesis, transport, metabolism and non-genomic actions, Testosterone Action, Deficiency, Substitution, 2004, pp. 1-38, Third Edition, Chapter 1, Cambridge University Press.
Sadjadi, S. et al., Analysis of Immunosuppressants from Whole Blood using Protein Precipitation and LC/MS/MS, Chromatography Today, Nov./Dec. 2013, pp. 20-23.
Sallustio, Benedetta C., LC-MS/MS for immunosuppressant therapeutic drug monitoring, Bioanalysis, 2010, 2 pp., vol. 2, No. 6 (abstract only).
Samskog, Jenny et al., Miniaturized on-line proteolysis-capillary liquid chromatography-mass spectrometry for peptide mapping of lactate dehydrogenase, Journal of Chromatography A, 2003, pp. 83-91, vol. 998.
Sargent, M. (Ed.), Guide to achieving reliable quantitative LC-MS measurement, RSC Analytical Methods Committee, 2013, 68 pp.
Singh, Ravinder J. et al., Quantitative Analysis of Testosterone in Serum by LC-MS/MS, Thermo Scientific Application Note: 429, 2017, 4 pp.
Tszyrsznic, Wlodzimierz et al., Two rapid ultra performance liquid chromatography/tandem mass spectrometry (UPLC/MS/MS) methods with common sample pretreatment for therapeutic drug monitoring of immunosuppressants compared to immunoassay, Journal of Chromatography B, 2013, pp. 9-15, vol. 928.

\* cited by examiner

GENERIC PRETREATMENT REAGENTS FOR ANALYTE DETERMINATIONS

CROSS-REFERENCE TO RELATED APPLICATIONS

This application is a continuation of International Application No. PCT/EP2018/057754 filed Mar. 27, 2018, which claims priority to European Application No. 17163332.4 filed Mar. 28, 2017, the disclosures of which are hereby incorporated by reference in their entirety.

SUMMARY OF THE INVENTION

The present invention relates to an in vitro method for releasing analytes from a sample comprising contacting said sample with (i) a chaotropic agent, (ii) an organic solvent, (iii) a detergent, and (iv) at least one agent providing bicarbonate ions. The present invention further relates to a release agent for releasing analytes from a sample comprising the aforesaid compounds. Moreover, the present invention relates to uses, kits, methods and devices related to the method and the release agent of the present invention.

BACKGROUND OF THE INVENTION

In vitro diagnostic (IVD) methods typically require a sample preparation step before performing the actual analysis. The sample preparation may imply several functions, like analyte release from the sample matrix, hemolysis in cases where analytes are entrapped within the erythrocytes (e.g. immunosuppressive drugs) and possibly analyte enrichment of low abundance analytes. Another important function of the sample preparation step is the removal of the sample matrix in order to avoid interferences; in particular blood and blood-derived samples consist of a highly concentrated and complex mixture of proteins (albumins, immunoglobulins) and other biomolecules which may lead to problems in downstream analysis, e.g. obstruction or clogging of chromatography columns reducing their lifetime (Furey et al (2013) Talanta 115: 104), "drown out" or suppression of MS signals from the low-abundance analytes, and the like.

Mass spectrometry (MS), in particular liquid-chromatography tandem mass spectrometry (LC-MS/MS), has become the method of choice for analyte quantitation in in-vitro diagnostics. Especially in the case of the determination of small molecules having metabolites of similar structure, the specificity and accuracy of MS has become crucial for the generation of reliable results. Examples for such small molecules are vitamins like 25-hydroxy-vitamin D3, steroids like testosterone and immunosuppressive drugs like cyclosporine A and everolimus. 25-hydroxy-vitamin D3 and testosterone are determined from serum or plasma samples. In case of immunosuppressive drugs, the recommended matrix is whole blood, since these analytes are highly bound to erythrocytes (Al-Jenoobi, F I (2016), Austin Chromatography 3:1039; Sallustio, B C (2010), Bioanalysis 2:1141), thus requiring a hemolysis step before their quantification. For 25-hydroxy-vitamin D3, testosterone, cyclosporine A and everolimus it is also known that these analytes are bound to matrix proteins in the sample and require release from the matrix proteins before quantification: e.g. of cyclosporine A ("Personalized Immunosuppression in transplantation: role of biomarker monitoring and therapeutic drug monitoring", Oellerich & DasGupta (2016): Elsevier, Amsterdam) in blood, 50-70% are bound to erythrocytes, and of the cyclosporine A found in plasma, 98% is bound to lipoproteins, whereas only 2% is found free in plasma. Similarly, of everolimus (Oellerich & DasGupta, loc. cit.) in blood, approximately 75% are bound to erythrocytes, and of the everolimus found in plasma, 75% is bound to plasma proteins, whereas 25% is found free in plasma. 25-hydroxy-vitamin D3 and testosterone are practically exclusively bound to vitamin D binding protein and sex hormone-binding globulin, respectively (Package inserts for Elecsys Assay Vitamin D total (2014 November, V 5.0); Rommerts F F G (2004): "Testosterone: an overview of biosynthesis, transport, metabolism and non-genomic actions"; In: Nieschlag, E, Behre, H M (eds.): Testosterone action, deficiency, substitution, 3rd edition. Cambridge, Cambridge University Press, 1-38).

The sample preparation step, including the sample pretreatment reagent, is the first and the most critical part of method development in LC-MS/MS analysis and other IVD quantitation methods/assays, as it directly impacts on the accuracy of the analytical method (10). The most popular pretreatment method from the state-of-the-art is the treatment of the samples (serum-, plasma- or whole blood) with organic solvents like methanol or acetonitrile, sometimes also with sulfate salts like ZnSO4 as helping additive for precipitation, inducing an analyte release from the sample matrix and at the same time removal of matrix components by precipitation (Sallustio, B C, loc. cit.; Gomes et al. (2013), Bioanalysis 5: 3063; Package inserts for Elecsys Assays: Cyclosporine (2013 June, V 1.0), everolimus (2015 November, V 1.0), sirolimus (2015 December, V 1.0), tacrolimus (2014 November, V 3.0), and their ISD pretreatment reagent (2014 October, V 3.0); Sadjadi S (2013), Chromatography Today, November/December: 20). However, these methods require removal of a precipitate and are, therefore, not compatible with some downstream applications, e.g. bead-enrichment for LC-MS/MS; moreover, the organic solvent may inhibit analyte capture by the beads. Thus, bead enrichment LC-MS/MS methods typically require aqueous-based solutions for pre-analytics. Pretreatment reagents used for sample preparation in a bead enrichment workflow are ideally provided as stable and ready-to-use solutions. These solutions can be placed on-board of the instrument for a long period of time offering a workflow not needing user interactions. The use of reagents as lyophilisate is, however, necessary when chemically instable reagents are involved, which hampers the workflow by requiring manual handling steps for reconstitution, since manual handling steps generate additional costs and also provide sources for errors. In addition, the reconstituted reagent typically shows short shelf-life and has to be replaced by freshly prepared solutions.

Some pretreatment methods use saponification for analyte release from the matrix (Package inserts for Elecsys Assay Vitamin D total (2014 November, V 5.0); Gomes et al., loc. cit.), and consist of mixing the sample with a potassium-of sodium hydroxide solution. This pretreatment method often implies the addition of a reducing reagent like dithiothreitol (DTT) for opening disulfide bridges in the matrix proteins to be unfolded. An advantage here is that the denaturation of the matrix proteins takes place without the formation of any precipitates. However, since the reducing reagent is usually not chemically stable in alkaline solutions, two separate components, e.g. DTT and NaOH, have to be provided. The consequence is that more space is required on the analyzer and a 2-pipetting-step pretreatment is required.

Other assays use pretreatment reagents triggering a competitive displacement of the analyte to be determined by adding an excess of a structurally similar compound. For example, the Elecsys testosterone test contains 2-bromoestradiol in the immunoreagent in order to release testosterone from its binding proteins (Package inserts for Elecsys Assay Testosterone (2014 December, V 8.0). This method, however, may compromise a bead-enrichment workflow by occupying positions in the capture beads, thus reducing or limiting their capacity for capturing the analyte itself, possibly leading to analyte loss. The competing compound may also cause interferences in LC-MS/MS due to the similar structure, thus making a co-elution and ion-suppression very probable.

Also, proteolytic sample treatment can be used for the removal of the sample matrix and the analyte release (U.S. Pat. No. 7,964,363 B2; U.S. Pat. No. 8,221,986 B2). However, proteolysis reagents produce a multitude of peptide fragments from matrix proteins, which may hinder a bead-enrichment workflow by occupying precious bead positions. As a consequence, analyte capture by the beads is not possible in a complete manner leading to analyte and sensitivity loss. Furthermore, proteolytic pretreatment methods require usually more than one pipetting step with different reagents, which leads to more complex and time consuming workflows on the analyzer.

Chaotropic reagents are also known in the literature as reagents for protein denaturation and cell solubilization (Peterson P A (1971), J Biol Chem 246, 7748; Marston F A O (1990), Methods Enzymol, 182:264) and are applied as release reagents in assays (17). However, typical formulations use highly dosed reagents, with 6-8 M concentrations of urea or guanidine HCl, which often cause interferences in LC-MS/MS measurements (Samskog J (2003), J Chromatography A, 998:83; Antignac J P (2005, Anal Chim Acta, 529:129; Chiu M L (2010), JALA 15:233; Proc et al. (2010), J Proteome Res 9: 5422).

+ESI MRM Frag=380.0V CF=0.000 DF=0.000 CID@25.0 (292.2000→99.8000) testo lgc0001.d;

X-axis: Acquisition Time (sec); Y-axis: Counts×$10^2$

Figure 2:
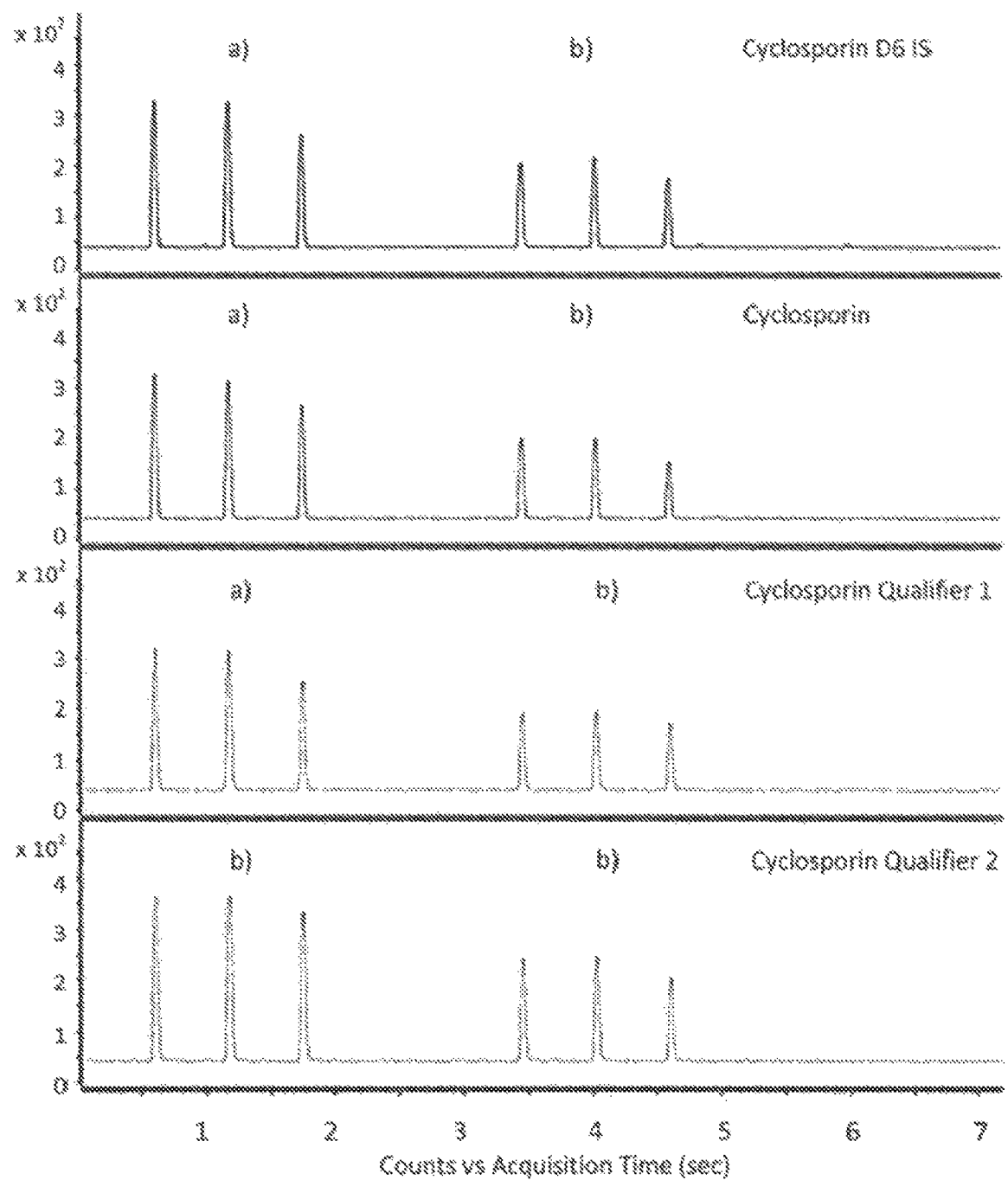

FIG. 2: LC-MS analysis of Cyclosporine (CSA) spiked at 64 ng/mL into analyte free human whole blood purified by enrichment bead workflow a) without pretreatment and b) with a pretreatment with F4.

Cyclosporin D6 IS: +ESI MRM Frag=380.0V CF=0.000 DF=0.000 CID@30.0 (1225.8500→1208.8500) cyclo lgc0002.d;

Cyclosporin: +ESI MRM Frag=380.0V CF=0.000 DF=0.000 CID@30.0 (1219.8500→1202.8500) cyclo lgc0002.d;

Cyclosporin Qualifier 1: +ESI MRM Frag=380.0V CF=0.000 DF=0.000 CID@61.0 (1208.8800→224.1000) cyclo lgc0002.d;

Cyclosporin Qualifier 2: +ESI MRM Frag=380.0V CF=0.000 DF=0.000 CID@33.0 (1202.8500→1184.8000) cyclo lgc0002.d;

X-axis: Acquisition Time (sec); Y-axis: Counts×$10^2$

Figure 3:
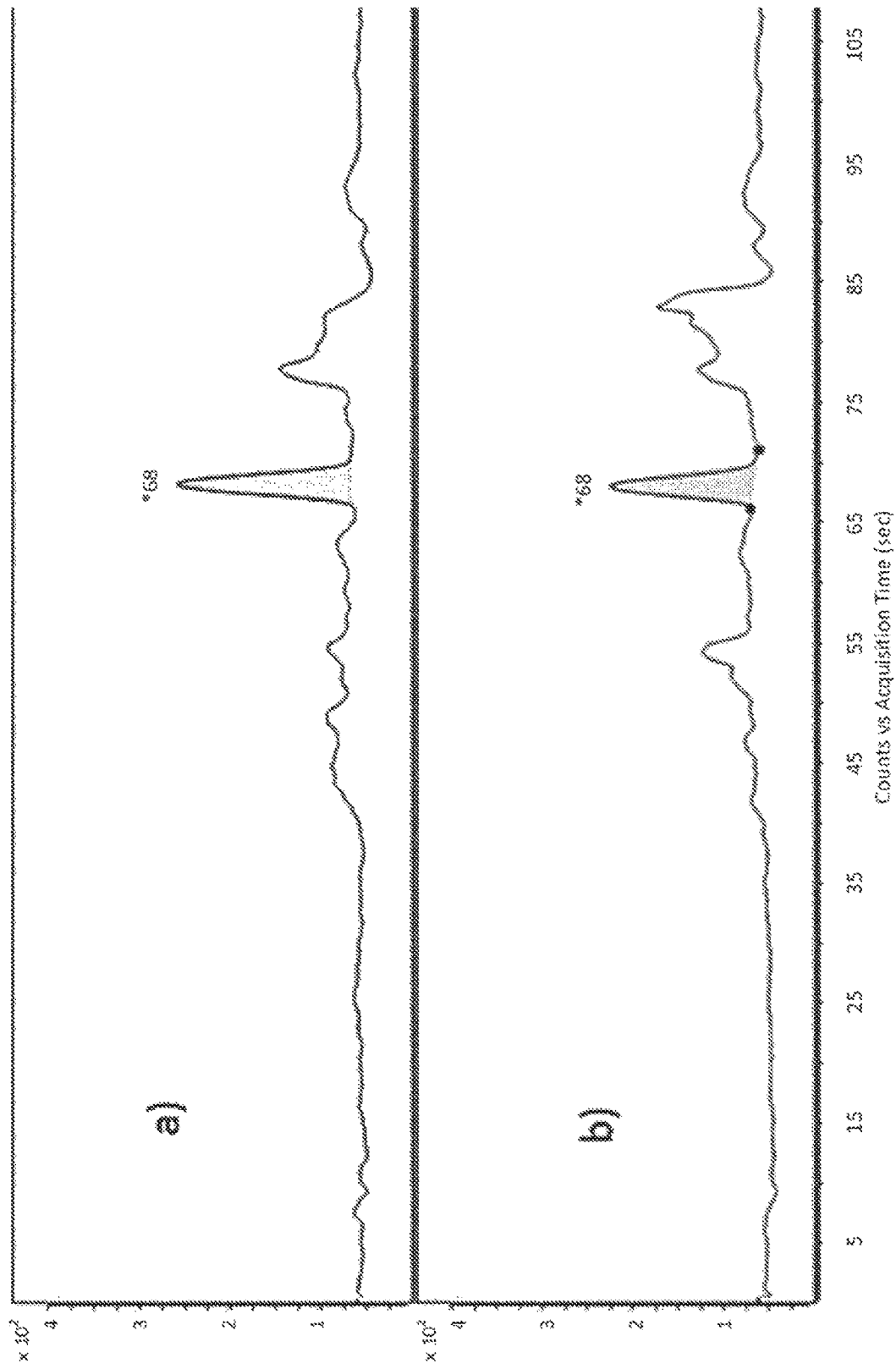

FIG. 3. LCMS analysis of Testosterone (Testo) spiked at 250 pg/mL into analyte free human serum purified by enrichment bead workflow a) without pretreatment and b) with a pretreatment with F4.

a) +ESI MRM Frag=380.0V CF=0.000 DF=0.000 CID@25.0 (289.2200→96.8000) sample 16.d;

b) +ESI MRM Frag=380.0V CF=0.000 DF=0.000 CID@25.0 (289.2200→96.8000) sample 4.d;

X-axis: Acquisition Time (sec); Y-axis: Counts×$10^2$

DETAILED DESCRIPTION OF THE INVENTION

There is, thus, a need in the art for improved means and methods for releasing analytes from samples, in particular for pretreatment reagent providing good extraction efficiency and not interfering with downstream applications such as bead enrichment. This problem is solved by the means and methods disclosed herein.

Accordingly, the present invention relates to an in vitro method for releasing analytes from a sample comprising contacting said sample with (i) a chaotropic agent, (ii) an organic solvent, (iii) a detergent, and (iv) at least one agent providing bicarbonate ions.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value ±20%, more preferably ±10%, most preferably ±5%.

The methods of the present invention are in vitro methods. Thus, in an embodiment, the methods are not performed on the human body. Also, the methods of the present invention, in an embodiment, are not diagnostic methods providing a diagnosis of a health state of a subject; it is, however, envisaged that the methods of the present invention, in an embodiment, provide information which the medical practitioner may find helpful in establishing a diagnosis or which may be considered in deciding on further treatment of a subject. Moreover, the methods may comprise steps in addition to those explicitly mentioned above. For example, further steps may relate, e.g., to providing a sample, e.g. a sample from a subject, in an embodiment obtained as described herein below; to contacting said sample with one or more further compounds as specified herein below; and/or to removing insoluble compounds after contacting the sample with said compounds. Moreover, one or more of the steps of the methods may be performed by automated equipment.

The term "sample", as used herein, refers to sample comprising or suspected to comprise at least one analyte. In an embodiment, the sample is a biological sample, in an embodiment a sample of a body fluid, a sample of separated cells, a sample from a tissue or an organ or a sample of wash/rinse fluid obtained from an outer or inner body surface. Samples can be obtained by well-known techniques and include scrapes, swabs and biopsies. Samples can be obtained by use of brushes, (cotton) swabs, spatulae, rinse/wash fluids, punch biopsy devices, puncture of cavities with needles or surgical instrumentation. Tissue or organ samples may be obtained from any tissue or organ by, e.g., biopsy or other surgical procedures. In an embodiment, the sample is a liquid sample, in a further embodiment is a sample of a body fluid, e.g., in an embodiment, blood, plasma, serum, urine, saliva, lacrimal fluid, and fluids obtainable from the breast glands, e.g. milk. In a further embodiment, the sample is a blood, plasma, or serum sample. Blood samples may be obtained by blood taking, e.g. by puncturing an arterial and/or a venous blood vessel. Plasma and serum samples may be obtained from blood samples according to well-known methods. In an embodiment, the sample is an EDTA plasma sample, in a further embodiment, the sample is an EDTA blood sample. The sample, in an embodiment, comprises or is suspected to comprise at least one analyte as specified elsewhere herein. As used herein, the term "sample" relates to the sample before it is contacted with the compounds as specified herein. During contacting, the term "release mixture" is used, as long as both the constituents of the sample and of the aforesaid compounds are present, whereas after contacting, i.e. after at least one of the constituents of the sample and/or of the aforesaid compounds was removed, the term "extract" is used. In an embodiment, the sample is a biological sample obtained from an individual for the purpose of evaluation in vitro. In a further embodiment the liquid sample is dried on a filter paper or membrane. In an embodiment the sample used herein refers to an aliquot of a sample obtained from an individual.

The term "contacting", as used in the context of the methods of the present invention, is understood by the skilled person. In an embodiment, the term relates to bringing a sample of the present invention in physical contact with at least the compounds as indicated and thereby allowing the sample and the compounds to interact. Contacting a sample to a multitude of compounds, e.g. a chaotropic agent, an organic solvent, a detergent, and at least one agent providing bicarbonate ions, may be achieved by successive addition of the single compounds, by successive addition of reagents comprising two or more of said compounds, e.g. by adding one reagent comprising the chaotropic agent and the at least one agent providing bicarbonate ions followed by adding a second reagent comprising the organic solvent and the detergent, or by contacting the sample with a release agent comprising all of the aforesaid compounds, in an embodiment with the release agent of the present invention. In any of the aforesaid cases, the sample is contacted to all four of the aforesaid compounds simultaneously, i.e. the sample is allowed to interact with all of the aforesaid compounds contacting the sample for at least the time frames as specified elsewhere herein. In case not all compounds are added simultaneously, the indicated incubation time starts when the last compound is added.

As used herein, the term "analyte" relates to a chemical compound present in a sample of a subject, in an embodiment, in a body fluid. In an embodiment, the analyte is a small molecule, i.e., in an embodiment, the analyte is not a biological macromolecule. In a further embodiment, the analyte is an organic molecule, in an embodiment a molecule comprising at least two contiguous carbon atoms. In an embodiment, the analyte is a molecule of the subject's metabolism. In a further embodiment, the analyte is a compound administered to said subject, e.g. in medical treatment, including prophylactic treatment. Also in an embodiment, the analyte is a low molecular weight chemical compound, in an embodiment with a molecular mass of less than 5000 Da, in an embodiment less than 2000 Da. In a further embodiment, the analyte is selected from the list consisting of a steroid hormone, an oligopeptide, a polyketide, and a vitamin.

In an embodiment, at least one analyte released is a steroid hormone. The term "steroid hormone" is known to the skilled person to relate to a compound having a structure comprising a steroid ring system and having hormone function in a subject. In an embodiment, the steroid hormone is a corticosteroid or a sex steroid, in an embodiment is a sex steroid. In an embodiment, the analyte is at least one of an androgen, an estrogen, and a progestogen, in a further embodiment is at least one of testosterone, dihydrotestosterone, and androstenedionein, in a further embodiment is testosterone.

In an embodiment, at least one analyte released is an oligopeptide. The term "oligopeptide", as used herein, includes all compounds comprising at least two amino acids connected via a peptide bond. In an embodiment, the oligopeptide comprises of from 2 to 50 amino acids, in an embodiment comprises of from 3 to 25 amino acids, in a further embodiment comprises of from 4 to 15 amino acids. In an embodiment, at least one of said amino acids is an alpha-amino acid, in an embodiment is an L-alpha-amino acid, in a further embodiment is a proteinogenic amino acid. As will be understood, the oligopeptide may comprise further chemical side chains, including, without limitation, methyl groups, ethyl groups, ethylene groups, keto groups, hydroxyl groups, cyclic alkyl groups, sugar residues, and the like. In an embodiment, the oligopeptide is an endogenous or a therapeutic oligopeptide. In a further embodiment, the oligopeptide is a cyclic oligopeptide, in an embodiment is a cyclic oligopeptide antibiotic, in an embodiment is cyclosporine.

In an embodiment, at least one analyte released is a "polyketide", which term is known to the skilled person and includes, in particular, macrolides, ansamycins, polyenes, tetracyclines, and related compounds. In an embodiment, the polyketide is a macrolide. The term "macrolide", as used herein, relates a class of compounds comprising a macrocyclic lactone structure. In an embodiment, the macrocyclic lactone ring comprises of from 8 to 50 ring atoms, in an embodiment of from 12 to 40 ring atoms, in a further embodiment of from 15 to 35 ring atoms. In an embodiment, the macrolide comprises 23 ring atoms, such as in tacrolimus and in pimecrolimus, or the macrolide comprises 31 ring atoms, such as in sirolimus, everolimus, and temsirolimus. As is understood by the skilled person, the macrolide may comprise further ring structures directly or indirectly attached to the macrocyclic lactone ring, and/or the lactone ring and potential further rings may, in addition to the at least one oxygen heteroatom, comprise further heteroatoms, in particular nitrogen atoms. Moreover, the macrolide may further comprise organic and/or inorganic side chains, including in particular methyl groups, ethyl groups, ethylene groups, keto groups, hydroxyl groups, cyclic alkyl groups, sugar residues, and the like. In an embodiment, at least one analyte is everolimus ((1R,9S,12S,15R,16E,18R,19R,21R, 23S,24E,26E,28E,30S,32S,35R)-1,18-dihydroxy-12-[(2R)-1-[(1S,3R,4R)-4-(2-hydroxyethoxy)-3-methoxycyclohexyl] propan-2-yl]-19,30-dimethoxy-15,17,21,23,29,35-hexamethyl-11,36-dioxa-4-azatricyclo [30.3.1.0$^{4,9}$] hexatriaconta-16,24,26,28-tetraene-2,3,10,14,20-pentone, CAS-number 159351-69-6), sirolimus ((1R,9S,12S,15R, 16E,18R,19R,21R,23S,24E,26E,28E, 30S,32S,35R)-1,18-dihydroxy-12-{(2R)-1-[(1S,3R,4R)-4-hydroxy-3-methoxy-cyclohexyl]-2-propanyl}-19,30-dimethoxy-15,17,21,23,29, 35-hexamethyl-11,36-dioxa-4-azatricyclo[30.3.1.04,9] hexatriaconta-16,24,26,28-tetraene-2,3,10,14,20-pentone, CAS number 53123-88-9), tacrolimus ((1R,9S,12S,13R, 14S,17R,18E,21S,23S,24R,25S,27R)-1,14-dihydroxy-12-[(1E)-1-[(1R,3R,4R)-4-hydroxy-3-methoxycyclohexyl] prop-1-en-2-yl ]-23,25-dimethoxy-13,19,21,27-tetramethyl-17-(prop-2-en-1-yl)-11,28-dioxa-4-azatricyclo [22.3.1.0$^{4,9}$] octacos-18-ene-2,3,10,16-tetrone, CAS number 104987-11-3), pimecrolimus ((1R,9S,12S,13R,14S,17R,18E,21S,23S, 24R,25S,27R)-12-[(1E)-1-[(1R,3R,4S)-4-chloro-3-methoxycyclohexyl]prop-1-en-2-yl ]-17-ethyl-1,14-dihydroxy-23,25-dimethoxy-13,19,21,27-tetramethyl-11, 28-dioxa-4-azatricyclo [22.3.1.0$^{4,9}$]octacos-18-ene-2,3,10, 16-tetrone, CAS number 137071-32-0), or temsirolimus ((1R,2R,4S)-4-[(2R)-2-[(1R,9S,12S,15R,16E,18R,19R, 21R,23S,24E,26E,28E,30S,32S,35R)-1,18-dihydroxy-19, 30-dimethoxy-15,17,21,23, 29,35-hexamethyl-2,3,10,14, 20-pentaoxo-11,36-dioxa-4-azatricyclo [30.3.1.0$^{4,9}$] hexatriaconta-16,24,26,28-tetraen-12-yl]propyl]-2-methoxycyclohexyl 3-hydroxy-2-(hydroxymethyl)-2-methylpropanoate, CAS number 162635-04-3). In an embodiment, the analyte is selected from everolimus, sirolimus, tacrolimus, pimecrolimus and temsirolimus, in an embodiment is selected from everolimus, sirolimus, and tacrolimus, in a further embodiment is everolimus, in an embodiment is sirolimus, in an embodiment is tacrolimus.

In an embodiment, at least one analyte released is a "vitamin", a term which is known to the skilled person to relate to an organic compound required by a subject in small amounts and which the subject's body is unable to synthesize. As is also known to the skilled person, the term "vitamin" is a species-specific classification, since, depending on the species, a chemical compound may be a vitamin, or not. In an embodiment, the vitamin is a vitamin for a human subject, i.e. is a human vitamin. In an embodiment, the analyte is one of vitamin A (Retinol), $B_1$(Thiamine), $B_2$ (Riboflavin), $B_3$ (Niacin), $B_5$ (Pantothenic acid), $B_6$ (Pyridoxine), $B_7$ (Biotin), $B_9$ (folic acid), $B_{12}$ (Cyanocobalamin), C (Ascorbic acid), Vitamin D (Cholecalciferol or Ergocalciferol), E (Tocopherol), and K (Phylloquinone). In an embodiment, the analyte is a hydrophobic vitamin, in an embodiment a hydrophobic human vitamin, in a further embodiment is a human A, B, or D vitamin, in a further embodiment is a vitamin D. In an embodiment, term "vitamin D" is to be understood to include all naturally occurring compounds which contain the backbone of vitamin D2 or the backbone of vitamin D3. In a further embodiment, the vitamin is a vitamin D3, in a further embodiment is 25-hydroxy-vitamin D3.

In an embodiment, a multitude of analytes is released from a sample according to the present invention. In an embodiment, at least 4, in an embodiment at least 10, in a further embodiment at least 100 analytes are released from the sample. In an embodiment, said analytes released comprise at least one, in an embodiment at least two, in a further embodiment at least three, in a further embodiment all of testosterone, cyclosporine, everolimus, and 25-hydroxy-vitamin D3.

The term "releasing analytes", as used herein, relates to bringing or maintaining analytes comprised in a sample in solution. As is understood by the skilled person, an analyte of the present invention may be present freely dissolved in a sample, or may be bound to a constituent of the sample, e.g. to a protein, to a membrane, be entrapped in a vesicle, or the like. According to the invention, the fraction of a particular analyte found soluble in the extraction solution after extraction is at least 50% of total analyte present in said sample, in an embodiment is at least 60%, in a further embodiment is at least 70%, in a further embodiment is at least 80, in a further embodiment is at least 90%. Thus, in an embodiment, the extraction efficiency of the method of the present invention is at least 50%, in an embodiment is at least 60%, in an embodiment is at least 70%, in a further embodiment is at least 80, in a further embodiment is at least 90%. In an embodiment, releasing analytes comprises destroying and/or dissolving biological membranes and/or comprises denaturing and/or precipitating proteins. As is understood by the skilled person, the term "denaturing a protein" relates to inducing a conformational state in said protein which is different from its natural conformation. In an embodiment, denaturing is unfolding a protein to release cofactors and/or other analytes bound by the protein. Thus, in an embodiment, denaturing a protein may include precipitation of said protein; however, denaturing a protein may also be unfolding and solubilizing a polypeptide.

As used herein, the term "subject" relates to a vertebrate. In an embodiment, the subject is a mammal, in a further embodiment, a mouse, rat, cat, dog, hamster, guinea pig, sheep, goat, pig, cattle, or horse. Still in a further embodiment, the subject is a primate. In a further embodiment, the subject is a human. In an embodiment, the subject is afflicted or suspected to be afflicted with a disease or condition associated with a measurable deviation from normal of at least one analyte. In a further embodiment, the subject receives medical treatment comprising administration of at least one analyte, in an embodiment, of at least one of a steroid hormone, an oligopeptide, a polyketide, and a vitamin. In a further embodiment, the subject receives medical treatment comprising administration of at least one of testosterone, cyclosporine, everolimus, and vitamin D3. In a further embodiment, the subject receives medical treatment comprising administration of at least one of cyclosporine and everolimus.

As used herein, the term "chaotropic agent" relates to a compound disrupting hydrogen bonding between water molecules and disrupting the tertiary structure of biological macromolecules. In an embodiment, the chaotropic agent comprises guanidinium ions, i.e. is guanidinium chloride or guanidinium thiocyanate, is thiourea, or is urea. In an embodiment, the chaotropic agent is an agent not comprising sulfur atoms. Thus, in an embodiment, the chaotropic agent comprises or is guanidinium chloride or urea, in a further embodiment comprises or is guanidinium chloride, in a further embodiment comprises or is urea. In an embodiment, the chaotropic agent is guanidinium chloride or urea, in a further embodiment is guanidinium chloride, in a further embodiment is urea. In an embodiment, the concentration of the chaotropic agent, in an embodiment of the guanidinium chloride, in a further embodiment of the urea, is of from 1 M to 4 M, in an embodiment of from 2 M to 3.5 M, wherein said concentrations are concentrations in the treated sample during said contacting.

The term "organic solvent", as used herein, relates to a compound, the molecules of which comprise at least one carbon atom and which is liquid under IUPAC standard ambient temperature and pressure conditions (temperature: 25° C., pressure: $10^5$ kPa). In an embodiment, the organic solvent has a boiling point of at least 50° C., in an embodiment of at least 60° C., in a further embodiment at least 70° C., in a further embodiment at least 80° C. In an embodiment, the organic solvent is a neutral organic solvent, in a further embodiment is an aprotic solvent. In an embodiment, the organic solvent is a polar solvent, in an embodiment an aprotic polar solvent. In an embodiment, the organic solvent has a dipole moment of at least 1.5D, in an embodiment at least 2D, in a further embodiment at least 2.5 D, in a further embodiment at least 3D. In an embodiment, the organic solvent is selected from ethyl acetate, acetone, dimethylformamide, dimethyl sulfoxide, propylene carbonate, and acetonitrile, in a further embodiment is acetonitrile. In an embodiment, the concentration of said organic solvent, in an embodiment of acetonitrile, is of from 2% (v/v) to 20% (v/v), in an embodiment of from 3% (v/v) to 15% (v/v), in an embodiment of from 5% (v/v) to 10% (v/v), wherein said concentrations are concentrations in the treated sample during said contacting.

As used herein, the term "detergent" relates to an amphiphilic compound decreasing the surface tension of water in principle well-known to the killed person. In an embodiment, the detergent is a mixture of amphiphilic compounds; in a further embodiment, the detergent is a single amphiphilic compound, i.e. is a surfactant. In an embodiment, the detergent comprises, in an embodiment consists of, non-ionic surfactants. In a further embodiment, the detergent is a non-ionic surfactant. In an embodiment, the detergent comprises or is a polyethylene glycol alkyl ether, a polypropylene glycol alkyl ether, a polyoxyethylene glycol sorbitan alkyl ester, a polyethylene glycol octylphenyl ethers, a polyethylene glycol alkylphenyl ether, a glycerol alkyl ester, or a glycoside alkyl ether. In an embodiment, the glycoside alkyl ether is an alkyl-glycoside with an alkyl chain having of from 5 to 12 carbon atoms, in a further embodiment is an alkyl-glucoside with an alkyl chain having of from 5 to 12 carbon atoms, in a further embodiment is an octyl glycoside. In a further embodiment, the detergent comprises or is an alkyl-glycoside, in an embodiment is lauryl glucoside, decyl glucoside, or octyl-glucoside, in a further embodiment is an octyl-glucoside, in a further embodiment is β-D-Octyl-glucoside ((2R,3S,4S,5R,6R)-2-(hydroxymethyl)-6-octoxyoxane-3,4,5-triol, CAS No: 29836-26-8). In an embodiment, the concentration of the detergent is of from 0.2% (w/v) to 20% (w/v), in an embodiment of from 0.3% (w/v) to 2% (w/v), wherein said concentrations are concentrations in the treated sample during said contacting.

As used herein, the term "agent providing bicarbonate ions" includes any chemical compound being in chemical equilibrium with bicarbonate ions in an aqueous solution at pH 7. A "bicarbonate ion" (hydrogen carbonate ion) according to the present invention is an anion with the empirical formula $HCO_3^-$, formally having a molecular mass of 61.01 Daltons. Bicarbonate ions can be provided by a chemical compound containing at least one hydrogen carbonate or carbonate salt and/or by a chemical compound capable of releasing bicarbonate ions upon hydrolysis. A "carbonate salt", according to the present invention, is a chemical compound comprising carbonate ions; in an embodiment, the carbonate salt is a soluble carbonate salt, in particular is sodium carbonate ($Na_2CO_3$), potassium carbonate ($K_2CO_3$), or ammonium carbonate (($NH_4)_2CO_3$). A "hydrogen carbonate salt", according to the present invention, is a compound comprising $HCO_3^-$ ions, in an embodiment selected from the group consisting of sodium hydrogen carbonate ($NaHCO_3$), potassium hydrogen carbonate ($KHCO_3$), ammonium hydrogen carbonate ($NH_4HCO_3$), calcium hydrogen carbonate ($Ca(HCO_3)_2$) and magnesium hydrogen carbonate ($Mg(HCO_3)_2$). A "chemical compound capable of releasing bicarbonate ions upon hydrolysis" according to an embodiment of the present invention is a carbonate ester. A "carbonate ester" according to the present invention is a carbonyl group flanked by two alkoxy groups. The general structure of these carbonates is $R^1O(C=O)OR^2$, with $R^1$ and $R^2$, being alkyl or cyclic alkyl, in an embodiment independently selected from methyl, ethyl, propionyl, and butyl, or $R^1$ and $R^2$ together forming an alkyl-bridge, in particular an ethylene group. Thus, there are cyclic carbonate esters (e.g. ethylene carbonate) or non-cyclic carbonate esters (e.g. dimethyl carbonate) as well as hydroxylated or halogenated derivatives thereof available.

As is understood by the skilled person, carbonates cause alkalization of aqueous solutions. Thus, in an embodiment, carbonate salts are used in particular for release of analytes insensitive to alkaline conditions. In a further embodiment, in particular in case an analyte sensitive to alkaline pH, e.g. a macrolide, shall be released the pH during the contacting step is adjusted, or, in an embodiment, a hydrogen carbonate salt or a carbonate ester may be used. Thus, in an embodiment, the agent providing bicarbonate ions is selected from the group consisting of sodium hydrogen carbonate, potassium hydrogen carbonate, ammonium hydrogen carbonate, calcium hydrogen carbonate and magnesium hydrogen carbonate. In a further preferred embodiment the hydrogen carbonate salt is selected from the group consisting of sodium hydrogen carbonate, potassium hydrogen carbonate and ammonium hydrogen carbonate. Further preferred the hydrogen carbonate salt is selected from the group consisting of sodium hydrogen carbonate and potassium hydrogen carbonate.

In an embodiment, the agent providing bicarbonate ions is a cyclic or non-cyclic carbonate ester or a hydroxylated or halogenated derivative thereof, respectively. In a further embodiment, the agent providing bicarbonate ions is a cyclic or non-cyclic carbonate ester or a halogenated derivative thereof, respectively. In a further embodiment, the cyclic or non-cyclic carbonate ester or the halogenated derivative thereof is selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one, 4,5-dichloro-1,3-dioxolan-2-one, 2,5-dioxohexanedioic acid dimethyl ester, 1,2 butylene carbonate, cis 2,3 butylene carbonate and trans 2,3 butylene carbonate. In a further embodiment, the cyclic or non-cyclic carbonate ester or the halogenated derivative thereof is selected from the group consisting of ethylene carbonate, dimethyl carbonate, propylene carbonate, vinylene carbonate, trimethylene carbonate, erythritol bis-carbonate, glycerol 1,2-carbonate, 4-chloro-1,3-dioxolan-2-one and 4,5-dichloro-1,3-dioxolan-2-one. In a further embodiment, the cyclic or non-cyclic carbonate ester is selected from the group consisting of ethylene carbonate, dimethyl carbonate, glycerol 1,2-carbonate, propylene carbonate and vinylene carbonate. In a further embodiment, the cyclic or non-cyclic carbonate ester is selected from the group consisting of ethylene carbonate, dimethyl carbonate, glycerol 1,2-carbonate and propylene carbonate. In a further embodiment, the cyclic or non-cyclic carbonate ester is selected from the group consisting of ethylene carbonate, dimethyl carbonate and glycerol 1,2-carbonate. In a further embodiment, the agent providing bicarbonate ions comprises or is a carbonate ester as specified above, in an embodiment comprises or is a cyclic carbonate ester, in an embodiment comprises or is ethylene carbonate (1,3-dioxolan-2-one, CAS No: 96-49-1).

In an embodiment, the concentration of bicarbonate ions formally provided by the at least one agent providing bicarbonate ions is of from 0.1 M to 2 M, in an embodiment of from 0.2 M to 0.5M, wherein said concentrations are concentrations in the treated sample during said contacting. As used herein, concentration indications for bicarbonate ions are provided on a formal basis, assuming that all $CO_3$-units of the respective agent providing bicarbonate ions are present as bicarbonate ions, in an embodiment irrespective of pH; thus, e.g., a 0.1 M solution of a carbonate salt is assumed to provide bicarbonate ions at a concentration of 0.1 M; also, a 0.1 M solution of a carbonate ester is assumed to provide bicarbonate ions at a concentration of 0.1 M, irrespective of the degree of actual hydrolysis.

As will be understood by the skilled person, more than one agents providing bicarbonate ions can be arbitrarily mixed in order to achieve the effect disclosed in the present invention. Also, as the skilled person is aware of, in aqueous solution, bicarbonate ions are in equilibrium with carbon dioxide according to the following equations:

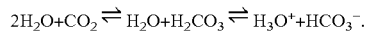

$$2H_2O + CO_2 \rightleftharpoons H_2O + H_2CO_3 \rightleftharpoons H_3O^+ + HCO_3^-.$$

Thus, salts of carbonic acid, i.e. carbonates and hydrogen carbonates, are in equilibrium with volatile carbon dioxide and are suitable in particular as agents providing bicarbonate ions in short- or midterm storage reagents. On the other hand, carbonate esters may in particular be considered for long-term storage reagents, in particular storage for at least 4 weeks, in an embodiment at least 2 months, in a further embodiment for at least 3 months, in a further embodiment for at least 6 months.

Surprisingly, it was found in the work underlying the present invention, that by including agent providing bicarbonate ions in the release mixture (pretreatment mixture), the concentration of chaotropic agent may be reduced, without adversely affecting extraction efficiency. Thus, in an embodiment, the sum of concentrations of (i) said chaotropic agent and (ii) bicarbonate ions formally provided by said at least one agent providing bicarbonate ions is at least 1.5 M, in an embodiment is of from 1.5 M to 4 M.

As noted above, analytes and efficiency of their extraction may be sensitive to extreme pHs, in particular if contacted for extended time periods. Thus, the pH during the contacting step is, in an embodiment, of from 3 to 9, in an embodiment of from 4 to 8, in a further embodiment of from 5 to 7.5. In an embodiment, the pH during the contacting step is 6.5±1.5, in a further embodiment is 6.5±1, in a further embodiment is 6.5±0.5, in a further embodiment is 6.5±0.3. Further, analytes and efficiency of their extraction may be sensitive to temperature deviations, in particular if contacted for extended time periods. Thus, in an embodiment, the contacting step is, in an embodiment, performed at a temperature of at most 50° C., in an embodiment at most 45° C., in a further embodiment at most 40°. In an embodiment the contacting step is performed at a temperature of at least 0° C., in an embodiment at least 10° C., in a further embodiment at least 20°, in a further embodiment at least 25° C., in a further embodiment at least 30° C. Thus, in an embodiment, contacting step is performed at a temperature of from 10° C. to 50° C., in and embodiment of from 20° C. to 45° C., in a further embodiment of from 25° C. to 40° C., in a further embodiment of 37° C.±2° C., in a further embodiment of about 37° C., in a further embodiment of 37° C. In an embodiment, the contacting step is performed for at most 1 h, in an embodiment at most 30 min, in a further embodiment at most 20 min. In an embodiment, the contacting step is performed for at least at least 2 min, in an embodiment at least 3 min, in a further embodiment at least 5 min, in a further embodiment at least 8 min, in a further embodiment at least 12 min. Thus, in an embodiment, the contacting step is performed for of from 2 to 30 min, in an embodiment of from 3 to 20 min, in a further embodiment of from 5 to 15 min. The skilled person is able to validate suitability of conditions as indicated above for releasing an analyte of interest, e.g. by incubating the analyte of interest under the intended conditions and determining the amount of analyte of interest remaining after incubation. In an embodiment, the aforesaid conditions of pH and temperature are maintained for the whole procedure, i.e. in an embodiment, while the method for releasing analyte is performed, in a further embodiment while the method for determining at least one analyte is performed.

The method for releasing analytes may also comprise contacting the sample to further agents. E.g., in an embodiment, the release mixture may further comprise a reducing agent, e.g. a thiol or other agent reducing disulfide bonds in proteins, in particular 2-Mercaptoethanol, 2-Mercaptoethylamine-HCl, TCEP, Cysteine-HCl, Homocysteine-HCl, Dithiothreitol (DTT), Dithioerythrol (DTE), N-Methylmaleimide, Ellman's Reagent and 1,2-dithiolane-3-carboxylic acid. Further, in an embodiment, a pH-stabilizing agent, e.g. a buffer, may be included.

Advantageously, it was found in the work underlying the present invention that by contacting a sample, in particular a blood or blood-derived sample, with the compounds of the present invention, a particularly broad range of chemical compounds, including compounds known in the art to be difficult to extract, such as vitamin D, can be extracted with high efficiency. Thus, the present invention provides for a highly efficient generic extraction method and corresponding reagents, which are particularly well suited for extracting steroid hormones, oligopeptides, polyketides, and vitamins, in particular in case members of two or more of the aforesaid compound classes shall be extracted simultaneously. Moreover, it was found that by including an agent providing bicarbonate ions in the release mixture, the amount of chaotropic agent required for complete release could be significantly reduced, thus in particular avoiding problems in mass spectrometry, such as ion suppression.

The definitions made above apply mutatis mutandis to the following. Additional definitions and explanations made further below also apply for all embodiments described in this specification mutatis mutandis.

The present invention further relates to a release agent for releasing analytes from a sample comprising (i) a chaotropic agent, (ii) an organic solvent, (iii) a detergent, and (iv) at least one agent providing bicarbonate ions.

The term "release agent", as used herein, relates to a mixture comprising at least the chemical compounds as specified. In principle, the release agent may be provided in solid form, in an embodiment to be dissolved at an appropriate concentration or to be added directly to a sample by the user. In an embodiment, the release agent is an aqueous solution comprising at least the compounds as specified. In a further embodiment, the release reagent is a threefold concentrated solution, in an embodiment ready for use, i.e. provided for direct threefold dilution into a sample as specified herein, i.e. by combining one part of release agent with two parts of sample. As is understood by the skilled person, the release agent may also be provided at a different concentration ratio, e.g., in an embodiment, as a twofold, fourfold, or fivefold concentrate. The skilled person is able to establish a concentration factor for the release agent as appropriate for a specific application, taking into account in particular the solubility of the constituents of the release agent, but also the specific properties of the sample and of the analyte of interest. E.g. in case the analyte is highly concentrated in the sample, it may be suitable to provide a release agent requiring strong dilution of the sample, e.g. a 1.1 fold concentrated release agent. On the other hand, in case the analyte is expected to be present in the sample at low concentrations, higher concentration factors may be considered.

In an embodiment, the release agent is a threefold concentrated solution. Accordingly, in an embodiment, the concentration of the chaotropic agent in the release agent, in particular in a threefold concentrated release agent, is of from 2 M to saturated, in an embodiment of from 2.5 M to 6 M. In a further embodiment, the concentration of the organic solvent in the release agent, in particular in a threefold concentrated release agent, is of from 2% (v/v) to 30% (v/v), in an embodiment of from 5% (v/v) to 20% (v/v), in an embodiment of from 15% (v/v) to 20% (v/v). In a further embodiment, the concentration of the detergent in the release agent, in particular in a threefold concentrated release agent, is of from 0.5% (w/v) to 20% (w/v), in an embodiment of from 1% (w/v) to 3% (w/v). In a further embodiment, the concentration of bicarbonate ions formally provided by the least one agent providing bicarbonate ions in the release agent, in particular in a threefold concentrated release agent, is of from 0.1 M to 6 M, in an embodiment of from 0.5 M to 2 M. In a further embodiment, the sum of concentrations of (i) the chaotropic agent and (ii) bicarbonate ions formally provided by said at least one agent providing bicarbonate ions in the release agent, in particular in a threefold concentrated release agent, is at least 2 M, in an embodiment is of from 3 M to 8 M. Thus, in an embodiment, in the release agent, in particular in a threefold concentrated release agent, the concentration of the chaotropic agent is of from 2 M to saturated, in an embodiment of from 2.5 M to 6 M; the concentration of the organic solvent is of from 2% (v/v) to 30% (v/v), in an embodiment of from 5% (v/v) to 20% (v/v), in an embodiment of from 15% (v/v) to 20% (v/v); the concentration of the detergent is of from 0.5% (w/v) to 20% (w/v), in an embodiment of from 1% (w/v) to 3% (w/v); and the concentration of bicarbonate ions formally provided by the least one agent providing bicarbonate ions is of from 0.1 M to 6 M, in an embodiment of from 0.5 M to 2 M; and, optionally, the sum of concentrations of (i) the chaotropic agent and (ii) bicarbonate ions formally provided by said at least one agent providing bicarbonate ions is at least 2 M, in an embodiment is of from 3 M to 8 M.

The release agent may comprise compounds in addition to the specified compounds. E.g. in an embodiment, a thiol compound, a buffer, or the like.

The present invention also relates to a use of a composition comprising (i) a chaotropic agent, (ii) an organic solvent, (iii) a detergent, and (iv) at least one agent providing bicarbonate ions, in an embodiment a release agent according to the present invention, and/or of the method for releasing analytes from a sample of the present invention for releasing at least one analyte from a sample.

Further, the present invention relates to a kit comprising (i) a chaotropic agent, (ii) an organic solvent, (iii) a detergent, and (iv) at least one agent providing bicarbonate ions, in an embodiment comprising the release agent of the present invention, comprised in a housing, in an embodiment further comprising least one detection agent for at least one analyte.

The term "kit", as used herein, refers to a collection of the aforementioned compounds, means or reagents of the present invention which may or may not be packaged together. The components of the kit may be comprised by separate housings (i.e. as a kit of separate parts), or two or more components may be provided in a single housing. Thus, the kit may comprise the compounds indicated as single compounds, e.g. as pure compounds for being dissolved by the user and/or as ready-to-use solutions. The kit may also comprise mixtures of two or more of the aforesaid compounds, e.g. a reagent comprising the chaotropic agent and the at least one agent providing bicarbonate ions and a second reagent comprising the organic solvent and the detergent, or the kit may comprise a reagent comprising all of the aforesaid compounds, in particular may comprise the release agent of the present invention. Moreover, it is to be understood that the kit of the present invention, in an embodiment, is to be used for practicing the method for releasing analytes from a sample and or the method for determining at least one analyte in a sample referred to herein. It is, in an embodiment, envisaged that components are provided in a ready-to-use manner for practicing the methods referred to herein. In an embodiment, all or some of said compounds are provided in concentrated liquid form wherein the concentrated component is diluted using a liquid such as an aqueous buffered solution or water as specified elsewhere herein. Further, the kit, in an embodiment, contains instructions for carrying out said methods. The instructions can be provided by a user's manual in paper- or electronic form. In addition, the manual may comprise instructions for interpreting the results obtained when carrying out the aforementioned methods using the kit of the present invention. In an embodiment, the kit further comprises water, a buffer, and/or suitable containers for performing the method.

The kit may further comprise a detection agent for at least one analyte. The term "detection agent", as used herein, relates to any agent assisting in detection of an analyte. Thus, the detection agent may be a chemical compound interacting or undergoing a chemical reaction with the analyte. In an embodiment, the detection agent is a chemical molecule binding, directly or indirectly, to the analyte of the present invention. As will be understood by the skilled person, the detection agent may also be an indirect detection agent, i.e. a detection agent not contacting the analyte directly, but by means of a further compound which itself binds to the analyte. In an embodiment, the detection agent is a direct detection agent, i.e. is an agent directly binding to the analyte. In an embodiment, the detection agent is an antibody, in an embodiment is an IgG. In an embodiment, the detection agent is a monoclonal antibody. In a further embodiment, the detection agent is an antibody bound to an indicator compound, i.e. to a compound whose presence in a sample can be detected by means known to the skilled person. Known indicator compounds include dyes, electrochemically active groups, or beads like latex beads. In an embodiment, the kit further comprises an extraction vessel, which may be a vessel for a single extraction, e.g. a plastic tube or an Eppendorf cup, or a device for a multitude of extractions, in particular a multi-well plate, e.g., a 96-well plate. In an embodiment, the extraction vessel may comprise a predetermined amount or volume of the release reagent of the present invention; e.g. in an embodiment, a predetermined volume may be provided in the wells of a multi-well plate or may be dried into said wells.

The present invention also relates to a method for determining at least one analyte in a sample comprising (a) releasing said analyte according to the method for releasing analytes from a sample according to the present invention to generate an extract;

(b) determining said released analyte in said extract; and, thereby (c) determining said analyte in a sample.

The term "determining", as used herein, refers to determining at least one characteristic feature of an analyte to be determined in an extract obtained from the sample. Characteristic features in accordance with the present invention are features which characterize the physical and/or chemical properties including biochemical properties of an analyte. Such properties include, e.g., molecular weight, viscosity, density, electrical charge, spin, optical activity, color, fluorescence, chemiluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of an analyte by standard operations, e.g., mathematical calculations such as multiplication, division or logarithmic calculus. In an embodiment, the at least one characteristic feature allows the determination and/or chemical identification of the analyte and its amount. Accordingly, the characteristic value, in an embodiment, also comprises information relating to the abundance of the analyte from which the characteristic value is derived. For example, a characteristic value of an analyte may be a peak in a mass spectrum. Such a peak contains characteristic information of the analyte, i.e. the m/z information, as well as an intensity value being related to the abundance of the said analyte (i.e. its amount) in the extract.

An analyte comprised by a sample may be, in an embodiment, determined in accordance with the present invention quantitatively or semi-quantitatively. For quantitative determination, either the absolute or precise amount of the analyte will be determined or the relative amount of the analyte will be determined based on the value determined for the characteristic feature(s) referred to herein above. The relative amount may be determined in a case were the precise amount of an analyte can or shall not be determined. In said case, it can be determined whether the amount in which the analyte is present is enlarged or diminished with respect to a second sample comprising said analyte in a second amount. Quantitatively analysing an analyte, thus, also includes what is sometimes referred to as semi-quantitative analysis of an analyte.

Moreover, determining as used in the method of the present invention may, in an embodiment, include using a compound separation step prior to the analysis step referred to before. In an embodiment, said compound separation step yields a time resolved separation of the metabolites comprised by the sample. Suitable techniques for separation to be used in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. In an embodiment, LC and/or GC are chromatographic techniques to be envisaged by the method of the present invention. Suitable devices for such determination of analytes are also known in the art. In an embodiment, mass spectrometry is used for determining the analyte, in particular gas chromatography mass spectrometry (GC-MS), liquid chromatography mass spectrometry (LC-MS), direct infusion mass spectrometry or Fourier transform ion-cyclotron-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). As an alternative or in addition to mass spectrometry techniques, the following techniques may be used for compound determination: nuclear magnetic resonance (NMR), magnetic resonance imaging (MRI), Fourier transform infrared analysis (FT-IR), ultraviolet (UV) spectroscopy, refraction index (RI), fluorescent detection, radiochemical detection, electrochemical detection, light scattering (LS), dispersive Raman spectroscopy or flame ionization detection (FID). These techniques are well known to the person skilled in the art and can be applied without further ado. The method of the present invention shall be, in an embodiment, assisted by automation. For example, sample processing can be automated by robotics. Data processing and comparison is, in an embodiment, assisted by suitable computer programs and databases. Automation as described herein before allows using the method of the present invention in high-throughput approaches. Thus, in an embodiment, the method is a method for determining a multitude of analytes, in an embodiment wherein said multitude is at least two, in an embodiment at least four, in a further embodiment at least ten, in a further embodiment at least 25, in a further embodiment at least 50 analytes. In a further embodiment, the multitude of analytes is determined from one or from a multitude of extracts according to step a) of the method for determining at least one analyte.

Moreover, the at least one analyte can also be determined by a specific chemical or biological assay. Said assay shall comprise means which allow to specifically detect the at least one analyte in the sample. In an embodiment, said means are capable of specifically recognizing the chemical structure of the analyte or are capable of specifically identifying the analyte based on its capability to react with other compounds or its capability to elicit a response in a biological read out system (e.g., induction of a reporter gene). Means which are capable of specifically recognizing the chemical structure of an analyte are, in an embodiment, antibodies or other proteins which specifically interact with chemical structures, such as receptors or enzymes. Specific antibodies, for instance, may be obtained using the analyte as antigen by methods well known in the art. Antibodies as referred to herein include both polyclonal and monoclonal antibodies, as well as fragments thereof, such as Fv, Fab, and $F(ab)_2$ fragments that are capable of binding the antigen or hapten. Moreover, encompassed are single chain antibodies and nanobodies. Also included are humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the analyte are, in an embodiment, enzymes which are involved in the metabolic conversion of the said analyte. Said enzymes may either use the analyte as a substrate or may convert a substrate into the analyte. Moreover, said antibodies may be used as a basis to generate oligopeptides which specifically recognize the analyte. These oligopeptides shall, for example, comprise the enzyme's binding domains or pockets for the said analyte. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the analyte may also be determined based on its capability to react with other compounds, i.e. by a specific chemical reaction. Further, the analyte may be determined in a sample due to its capability to elicit a response in a biological read out system. The biological response shall be detected as read out indicating the presence and/or the amount of the analyte comprised by the sample. The biological response may be, e.g., the induction of gene expression or a phenotypic response of a cell or an organism. In an embodiment, the determination of the least one analyte is a quantitative process, e.g., allowing also the determination of the amount of the at least one analyte in the sample.

The present invention further relates to a device for determining an analyte in a sample comprising the release agent according to the present invention and/or configured to perform a method of the present invention.

The term "device", as used herein, relates to a system of means comprising at least the means described, operatively linked to each other as to allow the determination. How to link the means of the device in an operating manner will depend on the type of means included into the device. In an embodiment, the means are comprised by a single device. In an embodiment, the device comprises at least an analysis unit, said analysis unit being configured to perform extraction of at least one analyte from a sample; in an embodiment, the analysis unit comprises the release agent according to the present invention, and/or is configured to perform a method of the present invention. The analysis unit may also be configured to detect at least one analyte. Moreover, the device may further comprise an evaluation unit for evaluating data obtained from the analysis unit, e.g. data relating to determining an analyte. Thus, in an embodiment, the device further comprises an analysis unit adapted for determining at least one analyte and/or an evaluation unit adapted for calculating an amount and/or concentration of said analyte in said sample. Thus, in an embodiment, the device is an analytic device, in an embodiment an in vitro diagnostic device. The person skilled in the art will realize how to link the aforesaid means without further ado. In an embodiment, the device is adapted to include an additional feature as described herein.

In view of the above, the following embodiments are particularly envisaged:

1. An in vitro method for releasing analytes from a sample comprising contacting said sample with (i) a chaotropic agent, (ii) an organic solvent, (iii) a detergent, and (iv) at least one agent providing bicarbonate ions.

2. The method of embodiment 1, wherein the concentration of said chaotropic agent is of from 1 M to 4 M, in an embodiment of from 2 M to 3.5 M.

3. The method of embodiment 1 or 2, wherein the concentration of said organic solvent is of from 2% (v/v) to 20% (v/v), in an embodiment of from 3% (v/v) to 15% (v/v), in an embodiment of from 5% (v/v) to 10% (v/v).

4. The method of any one of embodiments 1 to 3, wherein the concentration of said detergent is of from 0.2% (w/v) to 20% (w/v), in an embodiment of from 0.3% (w/v) to 2% (w/v).

5. The method of any one of embodiments 1 to 4, wherein the concentration of bicarbonate ions formally provided by said at least one agent providing bicarbonate ions is of from 0.1 M to 2 M, in an embodiment of from 0.2 M to 0.5M.

6. The method of any one of embodiments 1 to 5, wherein the sum of concentrations of (i) said chaotropic agent and (ii) bicarbonate ions formally provided by said at least one agent providing bicarbonate ions is at least 1.5 M, in an embodiment is of from 1.5 M to 4 M.

7. The method of any one of embodiments 1 to 6, wherein said concentrations are concentrations in the treated sample during said contacting.

8. The method of any one of embodiments 1 to 7, wherein said sample is a biological sample, in an embodiment a biological sample from a subject.

9. The method of any one of embodiments 1 to 8, wherein said sample is a bodily fluid sample, in an embodiment a blood, plasma, or serum sample.

10. The method of any one of embodiments 1 to 9, wherein at least one of said analytes is a low molecular weight analyte, in an embodiment with a molecular mass of less than 5000 Da, in an embodiment less than 2000 Da.

11. The method of any one of embodiments 1 to 10, wherein said analytes comprise at least one of a steroid hormone, an oligopeptide, a polyketide, and a vitamin.

12. The method of any one of embodiments 1 to 11, wherein said analytes comprise at least two, in an embodiment at least three, in a further embodiment all of a steroid hormone, an oligopeptide, a polyketide, and a vitamin.

13. The method of any one of embodiments 1 to 12, wherein said steroid hormone is at least one of an androgen, an estrogen, and a progestogen, in an embodiment is testosterone.

14. The method of any one of embodiments 1 to 13, wherein said oligopeptide is an endogenous or therapeutic oligopeptide, in an embodiment is a cyclic oligopeptide, in an embodiment is a cyclic oligopeptide antibiotic, in an embodiment is cyclosporine.

15. The method of any one of embodiments 1 to 14, wherein said polyketide is a macrolide, in an embodiment at least one of an antibiotic macrolide and a immunosuppressive macrolide, in an embodiment is tacrolimus, sirolimus, or everolimus, in a further embodiment is everolimus 16. The method of any one of embodiments 1 to 15, wherein said vitamin is a human vitamin, in an embodiment is a hydrophobic human vitamin, in a further embodiment is a human A, B, or D vitamin, in a further embodiment is a vitamin D, in a further embodiment is a vitamin D3, in a further embodiment is 25-hydroxy-vitamin D3.

17. The method of any one of embodiments 1 to 16, wherein said analytes comprise at least one, in an embodiment at least two, in a further embodiment at least three, in a further embodiment all of testosterone, cyclosporine, everolimus, and 25-hydroxy-vitamin D3.

18. The method of any one of embodiments 1 to 17, wherein said chaotropic agent, organic solvent, detergent, and, optionally, cyclic carbonate ester, are provided from a threefold concentrated release agent, in an embodiment a release agent according to any one of embodiments 19 to 34.

19. A release agent for releasing analytes from a sample comprising
(i) a chaotropic agent, (ii) an organic solvent, (iii) a detergent, and (iv) at least one agent providing bicarbonate ions.

20. The release agent of embodiment 19, wherein said release agent is a threefold concentrated solution.

21. The release agent of embodiment 19 or 20, wherein the concentration of said chaotropic agent is of from 2 M to saturated, in an embodiment of from 2.5 M to 6 M.

22. The release agent of any one of embodiments 19 to 21, wherein the concentration of said organic solvent is of from 2% (v/v) to 30% (v/v), in an embodiment of from 5% (v/v) to 20% (v/v), in an embodiment of from 15% (v/v) to 20% (v/v).

23. The release agent of any one of embodiments 19 to 22, wherein the concentration of said detergent is of from 0.5% (w/v) to 20% (w/v), in an embodiment of from 1% (w/v) to 3% (w/v).

24. The release agent of any one of embodiments 19 to 23, wherein the concentration of bicarbonate ions formally provided by said at least one agent providing bicarbonate ions is of from 0.1 M to 6 M, in an embodiment of from 0.5 M to 2 M.

25. The release agent of any one of embodiments 19 to 24, wherein the sum of concentrations of (i) said chaotropic agent and (ii) bicarbonate ions formally provided by said at least one agent providing bicarbonate ions is at least 2 M, in an embodiment is of from 3 M to 8 M.

26. The method of any one of embodiments 1 to 18 or the release agent of any one of embodiments 19 to 25, wherein said chaotropic agent is an agent not comprising sulfur atoms.

27. The method of any one of embodiments 1 to 18 or the release agent of any one of embodiments 19 to 26, wherein said chaotropic agent is guanidine hydrochloride and/or urea, in an embodiment is guanidine hydrochloride.

28. The method of any one of embodiments 1 to 18 or the release agent of any one of embodiments 19 to 27, wherein said organic solvent is acetonitrile.

29. The method of any one of embodiments 1 to 18 or the release agent of any one of embodiments 19 to 28, wherein said detergent is a non-ionic detergent, in an embodiment is an alkyl-glycoside.

30. The method of any one of embodiments 1 to 18 or the release agent of any one of embodiments 19 to 29, wherein said detergent is an alkyl-glycoside with an alkyl chain having of from 5 to 12 carbon atoms, in a further embodiment is an alkyl-glucoside with an alkyl chain having of from 5 to 12 carbon atoms, in a further embodiment is an octyl glycoside, in a further embodiment is an octyl-glucoside, in a further embodiment is β-D-Octyl-glucoside ((2R,3S,4S,5R,6R)-2-(hydroxymethyl)-6-octoxyoxane-3,4,5-triol, CAS No: 29836-26-8).

31. The method of any one of embodiments 1 to 18 or the release agent of any one of embodiments 19 to 30, wherein said at least one agent providing bicarbonate ions comprises a cyclic carbonate ester, in an embodiment comprises or is ethylene carbonate (1,3-dioxolan-2-one, CAS No: 96-49-1).

32. The release agent of any one of embodiments 19 to 31, wherein said sample is a biological sample, in an embodiment a biological sample from a subject.

33. The release agent of any one of embodiments 19 to 32, wherein said sample is a bodily fluid sample, in an embodiment a blood, plasma, or serum sample.

34. The release agent of any one of embodiments 19 to 33, wherein said release agent is an aqueous solution.

35. Use of a composition comprising (i) a chaotropic agent, (ii) an organic solvent, (iii) a detergent, and (iv) at least one agent providing bicarbonate ions a release agent, in an embodiment a release agent according to any one of embodiments 19 to 34, and/or the method according to any one of embodiments 1 to 18 for releasing at least one analyte from a sample.

36. A kit comprising (i) a chaotropic agent, (ii) an organic solvent, (iii) a detergent, and (iv) at least one agent providing bicarbonate ions, in an embodiment comprising the release agent of the present invention, comprised in a housing, in an embodiment further comprising least one detection agent for at least one analyte.

37. A method for determining at least one analyte in a sample comprising
(a) releasing said analyte according to the method according to any one of embodiments 1 to 18 to generate an extract;
(b) determining said released analyte in said extract; and, thereby
(c) determining said analyte in a sample.

38. The method of embodiment 37, wherein said method is a method for determining a multitude of analytes.

39. The method of embodiment 37 or 38, wherein said multitude is at least two, in an embodiment at least four, in a further embodiment at least ten, in a further embodiment at least 25, in a further embodiment at least 50 analytes.

40. The method of any one of embodiments 37 to 39, wherein said multitude of analytes is determined from one or from a multitude of extracts according to step a).

41. A device for determining an analyte in a sample comprising the release agent according to any one of embodiments 19 to 34 and/or configured to perform the method according to any one of embodiments 1 to 18 and/or 37 to 40.

42. The device of embodiment 41, wherein said device is an analytic device, in an embodiment an in vitro diagnostic device.

43. The device of embodiment 41 or 42, wherein said device further comprises an analysis unit adapted for determining at least one analyte and/or an evaluation unit adapted for calculating an amount and/or concentration of said analyte in said sample.

44. The method according to any one of embodiments 1 to 18 or 37 to 40, wherein said contacting comprises contacting said sample at a pH of 6.5±0.3 to
(i) guanidinium chloride at a concentration of about 3.3 M, ethylene carbonate at a concentration of about 0.33 M, acetonitrile at a concentration of about 10% (v/v), and beta-octyl-glucoside at a concentration of about 1% (w/v);
(ii) guanidinium chloride at a concentration of about 1.3 M, ethylene carbonate at a concentration of about 0.33 M, acetonitrile at a concentration of about 10% (v/v), and beta-octyl-glucoside at a concentration of about 1% (w/v);
(iii) guanidinium chloride at a concentration of about 2 M, ethylene carbonate at a concentration of about 0.2 M, acetonitrile at a concentration of about 6% (v/v), and beta-octyl-glucoside at a concentration of about 0.6% (w/v); or
(iv) guanidinium chloride at a concentration of about 1.3 M, ethylene carbonate at a concentration of about 0.8 M, acetonitrile at a concentration of about 6% (v/v), and beta-octyl-glucoside at a concentration of about 0.6% (w/v).

45. The method according to any one of embodiments 1 to 18 or 37 to 40, wherein said contacting comprises contacting said sample at a pH of 6.5±0.3 to
  (i) guanidinium chloride at a concentration of 3.3 M, ethylene carbonate at a concentration of 0.33 M, acetonitrile at a concentration of 10% (v/v), and beta-octyl-glucoside at a concentration of 1% (w/v);
  (ii) guanidinium chloride at a concentration of 1.3 M, ethylene carbonate at a concentration of 0.33 M, acetonitrile at a concentration of 10% (v/v), and beta-octyl-glucoside at a concentration of 1% (w/v);
  (iii) guanidinium chloride at a concentration of 2 M, ethylene carbonate at a concentration of 0.2 M, acetonitrile at a concentration of 6% (v/v), and beta-octyl-glucoside at a concentration of 0.6% (w/v); or
  (iv) guanidinium chloride at a concentration of 1.3 M, ethylene carbonate at a concentration of 0.8 M, acetonitrile at a concentration of 6% (v/v), and beta-octyl-glucoside at a concentration of 0.6% (w/v).

46. The release agent of any one of embodiments 20 to 34, the kit of embodiment 36, or the device of any one of embodiments 41 to 43, wherein said release agent comprises
  (i) guanidinium chloride at a concentration of about 5 M, ethylene carbonate at a concentration of about 0.5 M, acetonitrile at a concentration of about 15% (v/v), and beta-octyl-glucoside at a concentration of about 1.5% (w/v);
  (ii) guanidinium chloride at a concentration of about 2 M, ethylene carbonate at a concentration of about 0.5 M, acetonitrile at a concentration of about 15% (v/v), and beta-octyl-glucoside at a concentration of about 1.5% (w/v);
  (iii) guanidinium chloride at a concentration of about 6 M, ethylene carbonate at a concentration of about 0.6 M, acetonitrile at a concentration of about 18% (v/v), and beta-octyl-glucoside at a concentration of about 1.8% (w/v); or
  (iv) guanidinium chloride at a concentration of about 4 M, ethylene carbonate at a concentration of about 2.4 M, acetonitrile at a concentration of about 18% (v/v), and beta-octyl-glucoside at a concentration of about 1.8% (w/v).

47. The release agent of any one of embodiments 20 to 34, the kit of embodiment 36, or the device of any one of embodiments 41 to 43, wherein said release agent comprises
  (i) guanidinium chloride at a concentration of 5 M, ethylene carbonate at a concentration of 0.5 M, acetonitrile at a concentration of 15% (v/v), and beta-octyl-glucoside at a concentration of 1.5% (w/v);
  (ii) guanidinium chloride at a concentration of 2 M, ethylene carbonate at a concentration of 0.5 M, acetonitrile at a concentration of 15% (v/v), and beta-octyl-glucoside at a concentration of 1.5% (w/v);
  (iii) guanidinium chloride at a concentration of 6 M, ethylene carbonate at a concentration of 0.6 M, acetonitrile at a concentration of 18% (v/v), and beta-octyl-glucoside at a concentration of 1.8% (w/v); or
  (iv) guanidinium chloride at a concentration of 4 M, ethylene carbonate at a concentration of 2.4 M, acetonitrile at a concentration of 18% (v/v), and beta-octyl-glucoside at a concentration of 1.8% (w/v).

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Methods

Samples:
Samples for vitamin D (VitD): Human EDTA plasma, with 0 and 140 or 700 ng/mL VitD.
Samples for testosterone (Testo): Human EDTA plasma, 0 and 15 ng/mL Testo.
Samples for cyclosporine (CSA): Human EDTA whole blood, with 0 and 2000 ng/mL CSA.
Samples for everolimus (Eve): Human EDTA whole blood, and 0 and 30 ng/mL Eve.

Internal standard (IS):
10 µL IS per 100 µL sample, dissolved in human serum or EDTA plasma with 465 ng/mL VitD (25-hydroxy-vitamin D3, d6), 50 ng/mL Testo (testosterone, 3×C13), 6600 ng/mL CSA (cyclosporine, d4 and 3×C13), 100 ng/mL Eve (everolimus, d4 and 3×C13).

Procedure for Sample Pretreatment:
Eppendorf cups were used as pretreatment (PT) vessels. 100 µL sample (see above) was mixed with 10 µL internal standard (see above), vortexed for 10 seconds at room temperature (RT) and then incubated for 5 minutes at 37° C. on a shaker (1400 rpm). Then the indicated volume of PT reagent was added to the sample, vortexed for 10 seconds at RT and then incubated for a defined time period at 37° C. on a shaker (1400 rpm). Finally, the pretreated sample was assessed with respect to protein precipitation, hemolysis and analyte release, as described below.

Check of pretreated sample with respect to completeness of hemolysis and precipitation events: A qualitative assessment of PT reagents with respect to protein precipitation and whole blood hemolysis was performed. Protein precipitation and hemolysis were analyzed separately. For protein precipitation experiments, EDTA plasma was used as sample matrix. After performing the pretreatment, the pretreated sample was centrifuged for 20 minutes at RT (20000 g). The formulations were classified as suitable or as non-suitable by visual analysis. If a pellet was observed on the bottom of the cup, the formulation was classified as not suitable. For hemolysis assessment, whole blood (EDTA) was used as sample matrix. After performing the pretreatment, the pretreated sample was filled into a micro-hematocrit capillary and centrifuged for 30 minutes at RT (13000 rpm). The formulation was classified as not suitable for hemolysis when after centrifugation red blood cells were still observed. In cases where with a certain formulation either the hemolysis could not be obtained or precipitation was observed, no further assessment with respect to the degree of analyte release was performed.

Check of pretreated sample with respect to completeness of analyte release—direct Elecsys method:
After pretreating the samples, the quantitation of the analyte release was performed on Elecsys 2010 analyzer with commercial Elecsys assays (CSA, Everolimus, Testosterone, total Vitamin D) by own protocols omitting the Elecsys pretreatment step (CSA and everolimus via offline precipitation, total vitamin D via online denaturation, testosterone via R1 competitor). As controls for 0 or 100% analyte release the recoveries with samples containing free analytes (30% v/v acetonitrile/water with 0 and 700 ng/mL VitD; 1% aqueous octyl-ß-D-glucopyranosid with 0 and 15 ng/mL Testo; 100 mM ZnSO4 in methanol:ethyleneglycol 90:10 with 0 and 2000 ng/mL CSA; and 0 and 30 ng/mL Eve) were measured. Since strong matrix effects coming from the pretreated sample cause issues in Elecsys assays (e.g. lowering signal dynamic, deterioration of reproducibility and/or contamination of measuring cell) some countermeasures needed to be implemented. New Elecsys protocols with reduced pretreated sample (PT-S) volumes and increased reagent volumes were developed and used. In some cases, the matrix effect still interfered with the signal therefore the PT-S was diluted before measurement. The Elecsys measurements were performed in triplicates. Additionally, the measuring cell was cleaned regularly. Due to the imprecision of the modified Elecsys methods, formulations were classified as generating a "complete analyte release" already when showing recoveries >90%, and as acceptable when showing recoveries 80-90%. Good formulations show all 3 features: a complete analyte release, complete hemolysis and no precipitation.

Check of Pretreated Sample with Respect to Completeness of Analyte Release—LLE (liquid-liquid-extraction) Method:

After pretreating the samples, the PT-S was submitted to a LLE in order to reduce the matrix effects for the final analyte quantitation step with the Elecsys assays. 650 µL of organic solvent was added to the PT-S(n-hexane for VitD, Testo and CSA, ethyl acetate for Eve) and mixed gently for 3 minutes at room temperature (RT). After a short centrifugation (40 s at 21000 g, RT), 500 µL of the supernatant organic phase was transferred to an Eppendorf tube and evaporated at 30° C. in a speedvac to dryness. The dried extract was dissolved. CSA and Eve in 300 µL of the Elecsys ISD pretreatment reagent, 1:2 diluted with 0.9% NaCl solution; VitD in 100 µL 50% v/v acetonitrile/water followed dilution of 80 µL here-off with 180 µL human serum, VitD-depleted. Testo was dissolved in 30% v/v acetonitrile/water followed dilution of 50 µL here-off with 200 µL human serum, steroid-free. Finally, the solutions were measured on the Elecsys with the original assay protocols. As controls for 100% analyte release, the samples were also treated in parallel with a good working PT reagent, as determined with the direct Elecsys method mentioned above, and processed in analogy with the LLE method, and finally quantified on the Elecsys by using the original assay protocols. Due to the imprecision of the method, formulations were classified as generating a "complete analyte release" already when showing recoveries >90%, and as acceptable when showing recoveries 80-90%. Good formulations show all 3 features: a complete analyte release, complete hemolysis and no precipitation.

Example 2: Analyte Release

The first formulation "F" which was assessed according the methods described above and which yielded a complete analyte release and hemolysis without forming precipitates consisted of: 5M guanidine HCl (Gua), 0.5M Ethylene Carbonate (EtC), 15% ACN, 1.5% Octyl-ß-D-glucopyranosid (OßDG), pH6.5±0.3, 200 µL volume per 100 µL sample and 15 min incubation time at 37° C. (Table 1).

TABLE 1

F formulation, 200 µL volume per 100 µL sample and 15 min incubation time at 37° C.

|  | VitD | Testo | CSA | Eve |
| --- | --- | --- | --- | --- |
| Analyte release | >90% | >90% | >90% | >90% |
| Complete hemolysis | n.a. | n.a. | yes | yes |
| No precipitation | yes | yes | yes | yes |

It could be shown that the reagents can be exchanged by alternative reagents from the same class without affecting the function, and also yielded a complete analyte release and hemolysis without forming precipitates. The variants were also tested by using 200 µL PT reagent per 100 µL sample and 15 min incubation time at 37° C. (Table 2).

F-V1: 5M urea, 0.5M EtC, 15% ACN, 1.5% OßDG, pH6.5±0.3.
F-V2: 5M Gua, 0.5M propylene carbonate, 15% ACN, 1.5% OßDG, pH6.5±0.3.
F-V3: 5M Gua, 0.5M glycerol-1,2-carbonate, 15% ACN, 1.5% OßDG, pH6.5±0.3.
F-V4: 5M Gua, 0.5M EtC, 15% n-propanol, 1.5% OßDG, pH6.5±0.3.

TABLE 3

Variants of F, 200 µL volume per 100 µL sample and 15 min incubation time at 37° C.

|  |  | F-V1 | F-V2 | F-V3 | F-V4 |
| --- | --- | --- | --- | --- | --- |
| VitD | Analyte release | >90% | >90% | >90% | >90% |
|  | No precipitation | yes | yes | yes | yes |
| Testo | Analyte release | >90% | >90% | >90% | 88% |
|  | No precipitation | yes | yes | yes | yes |
| CSA | Analyte release | >90% | >90% | >90% | >90% |
|  | Complete hemolysis | yes | yes | yes | yes |
|  | No precipitation | yes | yes | yes | yes |
| Eve | Analyte release | >90% | >90% | >90% | >90% |
|  | Complete hemolysis | yes | yes | yes | yes |
|  | No precipitation | yes | yes | yes | yes |

Single components of F were down-titrated to show their impact on the pretreatment. The variants were also tested by using 200 µL PT reagent per 100 µL sample and 15 min incubation time at 37° C. (Table 3).

F-V5: 2.5M Gua, 0.5M EtC, 15% ACN, 1.5% OßDG, pH6.5±0.3.
F-V6: 1.25M Gua, 0.5M EtC, 15% ACN, 1.5% OßDG, pH6.5±0.3.
F-V7: 0.63M Gua, 0.5M EtC, 15% ACN, 1.5% OßDG, pH6.5±0.3.
F-V8: 0M Gua, 0.5M EtC, 15% ACN, 1.5% OßDG, pH6.5±0.3.
F-V9: 5M Gua, 0.25M EtC, 15% ACN, 1.5% OßDG, pH6.5±0.3.
F-V10: 5M Gua, 0.13M EtC, 15% ACN, 1.5% OßDG, pH6.5±0.3.
F-V11: 5M Gua, 0M EtC, 15% ACN, 1.5% OßDG, pH6.5±0.3.
F-V12: 5M Gua, 0.5M EtC, 30% ACN, 1.5% OßDG, pH6.5±0.3.
F-V13: 5M Gua, 0.5M EtC, 20% ACN, 1.5% OßDG, pH6.5±0.3.
F-V14: 5M Gua, 0.5M EtC, 10% ACN, 1.5% OßDG, pH6.5±0.3.
F-V15: 5M Gua, 0.5M EtC, 5% ACN, 1.5% OßDG, pH6.5±0.3.
F-V16: 5M Gua, 0.5M EtC, 0% ACN, 1.5% OßDG, pH6.5±0.3.

TABLE 3a

Variants of F, 200 µL volume per 100 µL sample and 15 min incubation time at 37° C.

|  | VitD AR/NPr | Testo AR/NPr | CSA AR/NPr/Hem | Eve AR/NPr/Hem |
| --- | --- | --- | --- | --- |
| F-V5 | >90%/yes | >90%/yes | >90%/yes/yes | >90%/yes/yes |
| F-V6 | >90%/yes | >90%/yes | >90%/yes/yes | >90%/yes/yes |

TABLE 3a-continued

Variants of F, 200 μL volume per 100 μL sample and 15 min incubation time at 37° C.

| | VitD AR/NPr | Testo AR/NPr | CSA AR/NPr/Hem | Eve AR/NPr/Hem |
|---|---|---|---|---|
| F-V7 | >90%/yes | >90%/yes | n.d./yes/no | n.d./yes/no |
| F-V8 | <80%/yes | >90%/yes | n.d./yes/no | n.d./yes/no |
| F-V9 | >90%/yes | >90%/yes | >90%/yes/yes | >90%/yes/yes |
| F-V10 | >90%/yes | >90%/yes | >90%/yes/yes | >90%/yes/yes |
| F-V11 | >90%/yes | >90%/yes | >90%/yes/yes | >90%/yes/yes |
| F-V12 | >90%/yes | >90%/yes | >90%/yes/yes | >90%/yes/yes |
| F-V13 | >90%/yes | >90%/yes | >90%/yes/yes | >90%/yes/yes |
| F-V14 | >90%/yes | >90%/yes | >90%/yes/yes | >90%/yes/yes |
| F-V15 | >90%/yes | >90%/yes | >90%/yes/yes | >90%/yes/yes |
| F-V16 | >90%/yes | >90%/yes | >90%/yes/yes | >90%/yes/yes |

(AR: analyte release, NPr: no protein precipitation; Hem: complete hemolysis)

Example 3: Bead Enrichment Interference

Formulation F shows interferences for Testo and CSA in the bead-enrichment-based LC-MS/MS analysis, i.e. loss of signal intensity by ion-suppression: During the optimization of the bead enrichment workflow, conditions for pretreatment of the samples were investigated using design of experiments. The read-out method for this study was a multiplexed HPLC method with a long chromatography step (7.5 min) and mass spectrometric detection. Reagent F was chosen as pretreatment reagent and the workflow conditions were as follows:

For serum (testosterone/25-OH vitamin D3): 100 μL Serum+100 μL PT-F; 50 μL Beads in 0.1% Ammoniumformate (25 mg/mL); Wash: 2× with ACN/H2O 5:95+5 mM NH$_4$OH; Elution: 100 μL ACN+2% FA.

Figure 1:
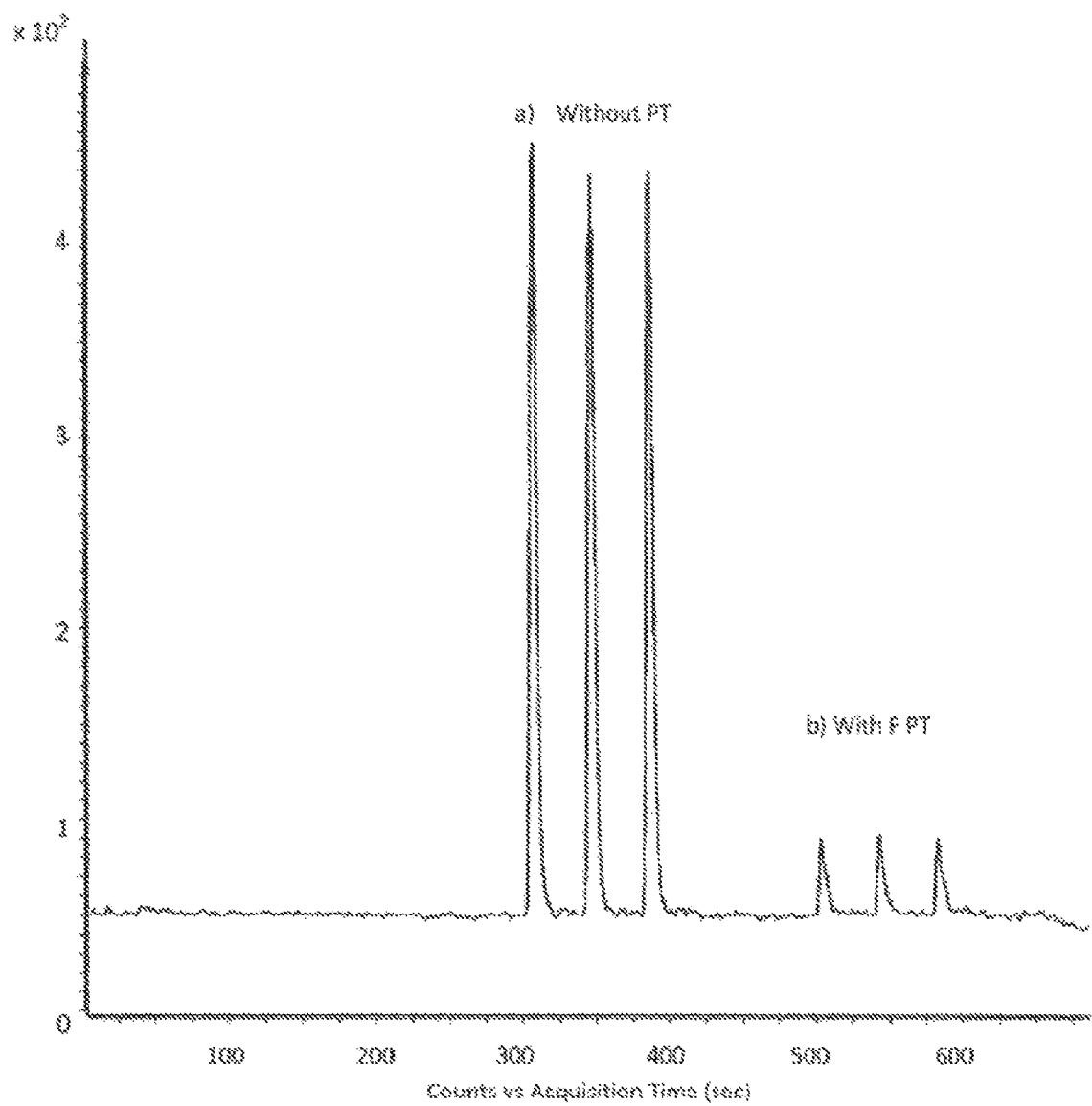
FIG. 1: Rapid LC-MS chromatograms of human serum sample prepared with enrichment beads a) without pretreatment (PT) and b) with F as pretreatment (PT) reagent and spiked with 0.7 ng/mL testosterone (Testo). Both samples, a) and b), are measured in triplicate.

For whole blood (cyclosporine/everolimus): 100 μL Sample+200 μL PT-F; 50 μL Beads in 15% ACN (25 mg/mL); Wash: 2× with ACN/H2O 35:65+5 mM NH$_4$OH; Elution: 100 μL ACN+2% FA Human samples were then prepared using these optimized workflows and spiked with analyte concentrations corresponding to the medical decision point. Analysis was performed using analyte-specific LC-MS methods with a fast chromatography step. The example (FIG. 1) shows the effect of a pretreatment step with the F reagent on the sensitivity of the LC-MS analysis of testosterone (Testo). Similar signal reduction was obtained for cyclosporine (CSA). Signal intensity for testosterone when using F as pretreatment was only approx. 10% of the analyte signal obtained without pretreatment. Without wishing to be bound by theory, this effect is most probably due to the fact that the washing procedure in the enrichment workflow was not sufficient to remove all traces of reagent after the pretreatment step. Residual guanidinium salt that was carried over through the workflow until the elution step could be the cause of strong ion suppression effects which led to sensitivity loss.

Formulations with Less Guanidine HCl, F4, F6:

Two further formulations, F4 and F6, containing less guanidine HCl were assessed according the methods described above and consisted of:

F4: 2M Gua, 0.5M EtC, 15% ACN, 1.5% OβDG, pH6.5±0.3, 200 μL volume per 100 μL sample and 15 min incubation time at 37° C.

F6: 0.5M Gua, 0.5M EtC, 15% ACN, 1.5% OβDG, pH6.5±0.3, 200 μL volume per 100 μL sample and 15 min incubation time at 37° C.

The results are shown in table 4. Shorter pretreatment times than the stated 15 min are possible. For F4 it was checked that also 3 min work well.

TABLE 4

F4 and F6, 200 μL volume per 100 μL sample and 15 min incubation time at 37° C.

| | | VitD | Testo | CSA | Eve |
|---|---|---|---|---|---|
| F4 | Analyte release | >90% | >90% | >90% | >90% |
| | Complete hemolysis | yes | yes | yes | yes |
| | No precipitation | yes | yes | yes | yes |
| F6 | Analyte release | >90% | >90% | n.d. | n.d. |
| | Complete hemolysis | yes | yes | no | no |
| | No precipitation | yes | yes | yes | yes |

These formulations do not show interferences in the bead-enrichment-based LC-MS/MS analysis.

The reduction of guanidine concentration had a positive effect on the analyte release or hemolysis of the samples. The effect of F4 on the LC-MS detection using fast chromatography was assessed using cyclosporine (CSA), testosterone (Testo) and vitamin D (VitD). The lower concentration of guanidine vs. F is beneficial for reducing the ion suppression effect. FIG. 2 shows that Cyclosporine could be measured by fast LC-MS after pretreatment using the reagent F4 without significant sensitivity loss compared to matrix extracted without pretreatment. Also for Testosterone it could be shown that no sensitivity loss was observed when pretreated/released with F4 (cf. FIG. 3) in contrast to the ion-suppression observed with F (cf. FIG. 1).

Example 4: Reagent Stability

The PT reagents were stressed at 35° C. for 3 weeks in the accelerated shelf-life study (ASL, 18-month shelf-life time model), and at 12° C. for up to 29 days in the on-board stability (OBS) study. In both studies the reagents were stressed in 2 mL micro tubes (polypropylene). The stressed ASL and OBS reagents and the corresponding non-stressed reagents (T0) were stored at −80° C. until their functional testing. The stressed and non-stressed PT reagents were tested by applying them in the sample pretreatment workflow (cf. above, 100 μL sample, 10 μL IS, pretreatment with 200 μL PT reagent for 15 min at 37° C.) followed by the measurement of recoveries of analyte release with the Elecsys procedure described above. The recovery value of stressed sample was compared with the non-stressed analogue (T0, 100%) and due to the imprecision of the modified Elecsys method, formulations were classified as stable already when showing recoveries ≥90%. Results are shown in Table 5.

TABLE 5

Recoveries in ASL & OBS of F/F4/F6, 200 μL volume per 100 μL sample and 15 min incubation time at 37° C.

| | | VitD | Testo | CSA | Eve |
|---|---|---|---|---|---|
| ASF | F | >90% | >90% | >90% | >90% |
| | F4 | >90% | >90% | >90% | >90% |
| | F6 | >90% | >90% | n.a. | n.a. |
| OBS | F | >90% | >90% | >90% | >90% |
| | F4 | >90% | >90% | >90% | >90% |
| | F6 | >90% | >90% | n.a. | n.a. |

(n.a.: not applicable since no complete hemolysis achievable)

Example 4: Decrease of Pretreatment Reagent Volume

A further formulation, F0, containing highest concentrations of single components was assessed according to the methods described above with respect to faster PT times and the use of lower volumes for the PT (see Table 6). F0 consisted of: 6M Gua, 0.6M EtC, 18% ACN, 1.8% OßDG, pH6.5±0.3. The tested times and volumes are depicted in Table 6; none of the tested conditions caused a precipitation. However, with volumes below 50 µL no complete hemolysis was achievable; therefore, the minimal volume tested for the determination of the analyte release was 50 µL. Selected conditions based on these results for follow-up experiments were:

F0: 6M Gua, 0.6M EtC, 18% ACN, 1.8% OßDG, pH6.5±0.3. 50 µL volume per 100 µL sample and 5 min incubation time at 37° C.

TABLE 6

Analyte release with F0, 100 µL sample and incubation at 37° C. with variable time & volume

| VitD | 10 µL F0 | 25 µL F0 | 35 µL F0 | 50 µL F0 |
|---|---|---|---|---|
| 0 min | <80% | <80% | <80% | >90% |
| 2.5 min | <80% | <80% | <80% | >90% |
| 15 min | <80% | <80% | <80% | >90% |
| Testo | 10 µL F0 | 25 µL F0 | 35 µL F0 | 50 µL F0 |
| 0 min | >90% | >90% | >90% | >90% |
| 2.5 min | >90% | >90% | >90% | >90% |
| 15 min | >90% | >90% | >90% | >90% |
| CSA | 50 µL F0 | 75 µL F0 | 100 µL F0 | |
| 0 min | >90% | >90% | >90% | |
| 2.5 min | >90% | >90% | >90% | |
| 15 min | >90% | >90% | >90% | |
| Eve | 50 µL F0 | 75 µL F0 | 100 µL F0 | |
| 0 min | 87% | >90% | >90% | |
| 2.5 min | >90% | >90% | >90% | |
| 15 min | >90% | >90% | >90% | |

Single components of F0 were down-titrated to show their impact on the pretreatment. The variants were also tested by using 50 µL PT reagent per 100 µL sample and 5 min incubation time at 37° C. (Table 7).

F0-V1: 4M Gua, 0.6M EtC, 18% ACN, 1.8% OßDG, pH6.5±0.3
F0-V2: 3M Gua, 0.6M EtC, 18% ACN, 1.8% OßDG, pH6.5±0.3.
F0-V3: 1M Gua, 0.6M EtC, 18% ACN, 1.8% OßDG, pH6.5±0.3.
F0-V4: 0M Gua, 0.6M EtC, 18% ACN, 1.8% OßDG, pH6.5±0.3.
F0-V5: 6M Gua, 0.3M EtC, 18% ACN, 1.8% OßDG, pH6.5±0.3.
F0-V6: 6M Gua, 0.15M EtC, 18% ACN, 1.8% OßDG, pH6.5±0.3.
F0-V7: 6M Gua, 0M EtC, 18% ACN, 1.8% OßDG, pH6.5±0.3.
F0-V8: 6M Gua, 0.6M EtC, 9% ACN, 1.8% OßDG, pH6.5±0.3.
F0-V9: 6M Gua, 0.6M EtC, 4.5% ACN, 1.8% OßDG, pH6.5±0.3.
F0-V10: 6M Gua, 0.6M EtC, 0% ACN, 1.8% OßDG, pH6.5±0.3.
F0-V11: 6M Gua, 0.6M EtC, 18% ACN, 0.9% OßDG, pH6.5±0.3.
F0-V12: 6M Gua, 0.6M EtC, 18% ACN, 0.45% OßDG, pH6.5±0.3.
F0-V13: 6M Gua, 0.6M EtC, 18% ACN, 0% OßDG, pH6.5±0.3.

TABLE 7

Variants of F0, 50 µL volume per 100 µL sample and 5 min incubation time at 37° C.

| | VitD AR/NPr | Testo AR/NPr | CSA AR/NPr/Hem | Eve AR/NPr/Hem |
|---|---|---|---|---|
| F0-V1 | <80%/yes | >90%/yes | >90%/yes/yes | 80%/yes/yes |
| F0-V2 | <80%/yes | >90%/yes | >90%/yes/yes | >90%/yes/yes |
| F0-V3 | <80%/yes | >90%/yes | >90%/yes/yes | >90%/yes/yes |
| F0-V4 | <80%/yes | >90%/yes | >90%/yes/yes | >90%/yes/yes |
| F0-V5 | >90%/yes | >90%/yes | >90%/yes | >90%/yes |
| F0-V6 | >90%/yes | >90%/yes | >90%/yes | >90%/yes |
| F0-V7 | >90%/yes | >90%/yes | >90%/yes | >90%/yes |
| F0-V8 | >90%/yes | >90%/yes | >90%/yes | >90%/yes |
| F0-V9 | >90%/yes | >90%/yes | >90%/yes | >90%/yes |
| F0-V10 | 85%/yes | >90%/yes | >90%/yes | >90%/yes |
| F0-V11 | >90%/yes | >90%/yes | >90%/yes | >90%/yes |
| F0-V12 | >90%/yes | >90%/yes | >90%/yes | >90%/yes |
| F0-V13 | <80%/yes | >90%/yes | >90%/yes | >90%/yes |

(AR: analyte release, NPr: no protein precipitation; Hem: complete hemolysis)

The influence of other pH values for F0 and other temperatures for the pretreatment with F0 was assessed. The variants were also tested by using 50 µL PT reagent per 100 µL sample and 5 min incubation time (Table 8). 60° C. lead to precipitations and crustification in vial borders.

F0-V14: 6M Gua, 0.6M EtC, 18% ACN, 1.8% OßDG, pH5.0. PT at 37° C.
F0-V15: 6M Gua, 0.6M EtC, 18% ACN, 1.8% OßDG, pH8.0. PT at 37° C.
F0-V16: 6M Gua, 0.6M EtC, 18% ACN, 1.8% OßDG, pH6.5±0.3. PT at 6° C.
F0-V17: 6M Gua, 0.6M EtC, 18% ACN, 1.8% OßDG, pH6.5±0.3. PT at 22° C.
F0-V18: 6M Gua, 0.6M EtC, 18% ACN, 1.8% OßDG, pH6.5±0.3. PT at 50° C.
F0-V19: 6M Gua, 0.6M EtC, 18% ACN, 1.8% OßDG, pH6.5±0.3. PT at 60° C.

TABLE 8

Variants of F0, 50 µL volume per 100 µL sample and 5 min incubation time at 37° C.

| | VitD AR/NPr | Testo AR/NPr | CSA AR/NPr/Hem | Eve AR/NPr/Hem |
|---|---|---|---|---|
| F0-V14 | >90%/yes | >90%/yes | >90%/yes/yes | >90%/yes/yes |
| F0-V15 | >90%/yes | >90%/yes | >90%/yes/yes | 84%/yes/yes |
| F0-V16 | >90%/yes | >90%/yes | >90%/yes/yes | <80%/yes/yes |
| F0-V17 | >90%/yes | >90%/yes | >90%/yes/yes | >90%/yes/yes |
| F0-V18 | >90%/yes | >90%/yes | <80%/yes/yes | >90%/yes/yes |
| F0-V19 | n.d./no | n.d./ no | n.d./no/yes | n.d./no/yes |

(AR: analyte release, NPr: no protein precipitation; Hem: complete hemolysis)

With the F0 variant F0-V7 it was found that no ethylene carbonate was required to achieve a complete analyte release. In the next step it was checked if ethylene carbonate helps to reduce the required amount of guanidine HCl in F0, thus giving the possibility to minimize its interference on the LC-MS/MS analysis (e.g. ion-suppression). Since VitD is the hardest case in term of analyte release, these experiments were performed with VitD only. Finally, with the working variant (F0-29) the other analytes were tested. The variants were tested by using 50 μL PT reagent per 100 μL sample and 5 min incubation time (Table 9); only for 2 variants (V26, V-27) the incubation time tested was 15 min.

F0-V20: 2M Gua, 0.6M EtC, 18% ACN, 1.8% OβDG, pH6.5±0.3.

F0-V21: 2M Gua, 1.2M EtC, 18% ACN, 1.8% OβDG, pH6.5±0.3.

F0-V22: 2M Gua, 2.4M EtC, 18% ACN, 1.8% OβDG, pH6.5±0.3.

F0-V23: 3M Gua, 0.6M EtC, 18% ACN, 1.8% OβDG, pH6.5±0.3.

F0-V24: 3M Gua, 1.2M EtC, 18% ACN, 1.8% OβDG, pH6.5±0.3.

F0-V25: 3M Gua, 2.4M EtC, 18% ACN, 1.8% OβDG, pH6.5±0.3.

F0-V26: 2M Gua, 2.4M EtC, 18% ACN, 1.8% OβDG, pH6.5±0.3. 15 min.

F0-V27: 3M Gua, 2.4M EtC, 18% ACN, 1.8% OβDG, pH6.5±0.3. 15 min.

F0-V28: 4M Gua, 0.6M EtC, 18% ACN, 1.8% OβDG, pH6.5±0.3.

F0-V29: 4M Gua, 2.4M EtC, 18% ACN, 1.8% OβDG, pH6.5±0.3.

TABLE 9

Variants of F0, 50 μL volume per 100 μL sample and 5 min incubation time at 37° C.

| | VitD AR/NPr | Testo AR/NPr | CSA AR/NPr/Hem | Eve AR/NPr/Hem |
|---|---|---|---|---|
| F0-V20 | <80%/yes | n.d. | n.d. | n.d. |
| F0-V21 | <80%/yes | n.d. | n.d. | n.d. |
| F0-V22 | <80%/yes | n.d. | n.d. | n.d. |
| F0-V23 | <80%/yes | n.d. | n.d. | n.d. |
| F0-V24 | <80%/yes | n.d. | n.d. | n.d. |
| F0-V25 | <80%/yes | n.d. | n.d. | n.d. |
| F0-V26 | <80%/yes | n.d. | n.d. | n.d. |
| F0-V27 | <80%/yes | n.d. | n.d. | n.d. |
| F0-V28 | <80%/yes | n.d. | n.d. | n.d. |
| F0-V29 | >90%/yes | >90%/yes | >90%/yes/yes | 81%/yes/yes |

(AR: analyte release, NPr: no protein precipitation; Hem: complete hemolysis)

As will be appreciated also from experiments with variants F-V11 and F0-V7 above, including an agent providing bicarbonate ions allows for reduction of concentration of chaotropic agent by a factor of approximately 2.

Furthermore, minimalistic formulations were assessed by taking only one component from F0, as well as two-component variant containing the solubilizers ACN or OβDG. The variants were tested by using 50 μL PT reagent per 100 μL sample and 5 min incubation time (Table 10).

F0-V30: 6M Gua

F0-V31: 0.6M EtC

F0-V32: 18% ACN

F0-V33: 1.8% OβDG

F0-V34: 6M Gua, 1.8% OβDG

F0-V35: 6M Gua, 18% ACN

F0-V36: 0.6M EtC, 1.8% OβDG

F0-V37: 0.6M EtC, 18% ACN

TABLE 10

Variants of F0, 50 μL volume per 100 μL sample and 5 min incubation time at 37° C.

| | VitD AR/NPr | Testo AR/NPr | CSA AR/NPr/Hem | Eve AR/NPr/Hem |
|---|---|---|---|---|
| F0-V30 | <80%/yes | >90%/yes | >90%/yes/yes | 87%/yes/yes |
| F0-V31 | <80%/yes | <80%/yes | n.d./yes/no | n.d./yes/no |
| F0-V32 | <80%/yes | >90%/yes | 86%/yes/yes | <80%/yes/yes |
| F0-V33 | <80%/yes | >90%/yes | n.d./yes/no | n.d./yes/no |
| F0-V34 | <80%/yes | >90%/yes | >90%/yes/yes | >90%/yes/yes |
| F0-V35 | <80%/yes | >90%/yes | >90%/yes/yes | >90%/yes/yes |
| F0-V36 | <80%/yes | >90%/yes | >90%/yes/yes | <80%/yes/yes |
| F0-V37 | <80%/yes | >90%/yes | n.d./yes/no | n.d./yes/no |

(AR: analyte release, NPr: no protein precipitation; Hem: complete hemolysis)

Example 5: Bead Workflow

The formulations F, F4 and F0 were checked in the bead-enrichment workflow. 100 μL sample (spiked serum with VitD, Testo, CSA and Eve) was equilibrated for 15 min at RT. Then PT reagent (F and F4: 200 μL; F0: 50 μL) was added to the sample and incubated (F and F4: 15 min; F0 5 min) at 37° C. After addition of 50 μL bead suspension (~2.5 mg beads) and equilibration for 5 minutes at RT a magnetic separation was performed. Two wash steps each containing 200 μL aqueous solution were carried out followed by the elution step with 100 μL acetonitrile (ACN)/2% aqueous formic acid (FA) 70/30 or acetonitrile/2% formic acid 98/2. After magnetic separation, 80 μL supernatant was mixed with 5 μL IS (in 50% methanol/water) of which 5 μL were injected and quantified by LC-MS/MS. For this study, the IS was added at the final step in order to determine the overall analyte yield after the workflow. The analyte recovery found in the bead-enrichment workflow depends on several parameters like used bead type for analyte capture (solid-phase extraction via size exclusion, reverse phase and/or ion exchange) and bead buffer composition, washing conditions, bead elution solvent, pretreatment reagent formulation and volume, pretreatment time. LC-MS/MS conditions: Column from Phenomenex, F5 (2.6 μm particle, 150×2.1 mm); 40° C. column temperature; gradient (see Table 11) with solvent A (2 mM ammonium acetate, 0.1% formic acid in water) and solvent B (2 mM ammonium acetate, 0.1% formic acid in 95% ACN plus 5% water); MS/MS with multi-reaction-monitoring.

TABLE 11

LC gradient

| Time (min) | Flow rate (μL/min) | A (%) | B (%) |
|---|---|---|---|
| 0.0 | 400 | 97 | 3 |
| 1.5 | 400 | 95 | 5 |
| 1.8 | 400 | 50 | 50 |
| 4.8 | 400 | 0 | 100 |
| 6.3 | 400 | 0 | 100 |
| 6.4 | 400 | 97 | 3 |
| 7.5 | 400 | 97 | 3 |

The results obtained for PT reagents F, F4 and F0 in combination with different bead types and different bead buffers are summarized in Table 13. Good or acceptable yields were obtained, especially with F4 and F0 in combination with analyte elution by ACN/2% FA 98/2.

TABLE 12

Analyte recoveries in enrichment-bead workflow and LC-MS/MS quantitation

| PT reagent/PT reagent volume/PT time/PT temperature | VitD | Testo | CSA | Eve |
|---|---|---|---|---|
| Workflow with elution by ACN/2% aqueous FA 70/30 | | | | |
| No PT | 0% | 55% | 42% | 8% |
| F: 5M Gua, 0.5M EtC, 15% ACN, 1.5% OβDG, pH 6.5 ± 0.3/ 200 μL/15 min/37° C. | 38% | 85% | 52% | 4% |
| F4: 2M Gua, 0.5M EtC, 15% ACN, 1.5% OβDG, pH 6.5 ± 0.3/200 μL/15 min/37° C. | 34% | 73% | 81% | 57% |
| Workflow with elution by ACN/2% FA 98/2 | | | | |
| No PT | <2% | 48% | 64% | 46% |
| F4: 2M Gua, 0.5M EtC, 15% ACN, 1.5% OβDG, pH 6.5 ± 0.3/200 μL/15 min/37° C./ 2 different bead types for SPE | 52-61% | 78-95% | >95% | 53-58% |
| F0: 6M Gua, 0.6M EtC, 18% ACN, 1.8% OβDG, pH 6.5 ± 0.3/50 μL/5 min/37° C./ Beads in 4 different buffers with different preservatives | 35-36% | 80-86% | 89-93% | 58-75% |

Example 6: Generic Formulations

Several PT reagents were found to be generic for the complete analyte release and hemolysis (in case of ISD) as well as showing no precipitation (see table 13). The formulations were stable and ready-to-use for a 1-step PT process and compatible with the bead-enrichment workflow. For reducing the potential of LC-MS/MS interferences such as ion-suppression and at the same time reducing the required reagent volumes for the PT, the formulation F0-V29 was developed.

TABLE 13

Generic PT formulations

| PT reagent | PT volume | PT time | Sample volume | PT temperature |
|---|---|---|---|---|
| F: 5M Gua, 0.5M EtC, 15% ACN, 1.5% OβDG, pH 6.5 ± 0.3 | 200 μL | 15 min | 100 μL | 37° C. |
| F-V11: 5M Gua, 15% ACN, 1.5% OβDG, pH 6.5 ± 0.3 | 200 μL | 15 min | 100 μL | 37° C. |
| F4: 2M Gua, 0.5M EtC, 15% ACN, 1.5% OβDG, pH 6.5 ± 0.3 | 200 μL | 3 or 15 min | 100 μL | 37° C. |
| F0: 6M Gua, 0.6M EtC, 18% ACN, 1.8% OβDG, pH 6.5 ± 0.3 | 50 μL | 5 min | 100 μL | 37° C. |
| F0-V7: 6M Gua, 18% ACN, 1.8% OβDG, pH 6.5 ± 0.3 | 50 μL | 5 min | 100 μL | 37° C. |
| F0-V29: 4M Gua, 2.4M EtC, 18% ACN, 1.8% OβDG, pH 6.5 ± 0.3 | 50 μL | 5 min | 100 μL | 37° C. |

The invention claimed is:

1. A release agent for releasing analytes from a sample comprising (i) a chaotropic agent, (ii) an organic solvent, (iii) a detergent, and (iv) at least one agent providing bicarbonate ions,
   wherein said chaotropic agent is guanidine hydrochloride and/or urea;
   wherein said organic solvent is acetonitrile;
   wherein said detergent is a non-ionic detergent; and
   wherein said at least one agent providing bicarbonate ions comprises a cyclic carbonate ester.

2. The release agent of claim 1, wherein said release agent is a threefold concentrated solution and
   wherein the concentration of said chaotropic agent is from 2 M to saturated;
   wherein the concentration of said organic solvent is from 2% (v/v) to 30% (v/v);
   wherein the concentration of said detergent is from 0.5% (w/v) to 20% (w/v); and
   wherein the formal concentration of bicarbonate ions is from 0.1 M to 6 M.

3. A kit comprising (i) a chaotropic agent, (ii) an organic solvent, (iii) a detergent, and (iv) at least one agent providing bicarbonate ions,
   wherein said chaotropic agent is guanidine hydrochloride and/or urea;
   wherein said organic solvent is acetonitrile;
   wherein said detergent is a non-ionic detergent; and
   wherein said at least one agent providing bicarbonate ions comprises a cyclic carbonate ester,
   wherein the components of the kit are provided in separate housings or two or more components are provided in a single housing.

4. The kit of claim 3, further comprising at least one detection agent for at least one analyte.

* * * * *